US011446559B2

(12) United States Patent
Ferrara et al.

(10) Patent No.: US 11,446,559 B2
(45) Date of Patent: Sep. 20, 2022

(54) SPORTS TRAINING SYSTEM

(71) Applicant: NEW TURF TECHNOLOGIES, INC., Los Angeles, CA (US)

(72) Inventors: Joseph Ferrara, Thousand Oaks, CA (US); Michael Kahn, Los Angeles, CA (US)

(73) Assignee: NEW TURF TECHNOLOGIES, INC., Los Angeles, CA (US)

( * ) Notice: Subject to any disclaimer, the term of this patent is extended or adjusted under 35 U.S.C. 154(b) by 0 days.

(21) Appl. No.: 16/153,620

(22) Filed: Oct. 5, 2018

(65) Prior Publication Data

US 2019/0105546 A1 Apr. 11, 2019

Related U.S. Application Data

(60) Provisional application No. 62/568,741, filed on Oct. 5, 2017.

(51) Int. Cl.
*A63B 102/18* (2015.01)
*A63B 21/00* (2006.01)
(Continued)

(52) U.S. Cl.
CPC ...... *A63B 69/0002* (2013.01); *A63B 21/4037* (2015.10); *A63B 60/46* (2015.10); *A63B 69/3661* (2013.01); *A63B 69/3667* (2013.01); *G06V 40/23* (2022.01); *G09B 19/0038* (2013.01); *G16H 20/30* (2018.01); *A63B 43/004* (2013.01); *A63B 43/005* (2013.01); *A63B 59/50* (2015.10); *A63B 69/0075* (2013.01); *A63B 69/0091* (2013.01); *A63B 69/3673* (2013.01);
(Continued)

(58) Field of Classification Search
CPC .......... A63B 69/3667; A63B 2069/367; A63B 69/0002; A63B 2069/0008
USPC .......................................... 473/270–273, 452
See application file for complete search history.

(56) References Cited

U.S. PATENT DOCUMENTS 3,979,116 A * 9/1976 Matchick ........... A63B 69/0002
434/247
4,463,950 A * 8/1984 Elkin ................. A63B 69/0002
473/451

(Continued)

OTHER PUBLICATIONS

International Search Report and Written Opinion, International Application No. PCT/US2018/054750 dated Feb. 5, 2019.

*Primary Examiner* — Jeffrey S Vanderveen
(74) *Attorney, Agent, or Firm* — Risso I.P.

(57) ABSTRACT

Described herein are devices and systems relating to sports training equipment, for example, for baseball. These devices and systems can comprise a mat with markers identifying a plurality of positions on the mat. In some embodiments, the system can comprise removably attachable footpads to identify ideal foot positions for an athletic performance. In some embodiments, the footpads comprise one or more pressure sensors. The system can comprise one or more position sensors on a ball, and one or more position sensors removably attachable to a hand-held sports instrument. In some embodiments, the system can comprise a memory, communicatively coupled to a processor and a camera, with executable instructions to implement a set-up component, a user recognition component, a practice component, and instructional component, and a play component.

12 Claims, 17 Drawing Sheets

(51) Int. Cl.

| | |
|---|---|
| *A63B 60/46* | (2015.01) |
| *A63B 71/02* | (2006.01) |
| *G06V 40/20* | (2022.01) |
| *G09B 19/00* | (2006.01) |
| *A63B 69/00* | (2006.01) |
| *A63B 69/36* | (2006.01) |
| *G16H 20/30* | (2018.01) |
| *A63B 102/02* | (2015.01) |
| *A63B 102/04* | (2015.01) |
| *A63B 102/06* | (2015.01) |
| *A63B 102/20* | (2015.01) |
| *A63B 102/32* | (2015.01) |
| *A63B 24/00* | (2006.01) |
| *A63B 43/00* | (2006.01) |
| *A63B 59/50* | (2015.01) |
| *A63B 69/38* | (2006.01) |
| *A63B 71/06* | (2006.01) |

(52) U.S. Cl.
CPC .......... *A63B 69/38* (2013.01); *A63B 71/0616* (2013.01); *A63B 71/0622* (2013.01); *A63B 71/0669* (2013.01); *A63B 2024/0068* (2013.01); *A63B 2024/0096* (2013.01); *A63B 2043/001* (2013.01); *A63B 2069/0008* (2013.01); *A63B 2069/367* (2013.01); *A63B 2071/024* (2013.01); *A63B 2071/065* (2013.01); *A63B 2071/0638* (2013.01); *A63B 2071/0647* (2013.01); *A63B 2071/0663* (2013.01); *A63B 2071/0666* (2013.01); *A63B 2071/0694* (2013.01); *A63B 2102/02* (2015.10); *A63B 2102/04* (2015.10); *A63B 2102/065* (2015.10); *A63B 2102/18* (2015.10); *A63B 2102/182* (2015.10); *A63B 2102/20* (2015.10); *A63B 2102/32* (2015.10); *A63B 2209/00* (2013.01); *A63B 2209/08* (2013.01); *A63B 2209/10* (2013.01); *A63B 2210/50* (2013.01); *A63B 2220/13* (2013.01); *A63B 2220/16* (2013.01); *A63B 2220/30* (2013.01); *A63B 2220/31* (2013.01); *A63B 2220/52* (2013.01); *A63B 2220/56* (2013.01); *A63B 2220/806* (2013.01); *A63B 2220/833* (2013.01); *A63B 2225/093* (2013.01); *A63B 2225/20* (2013.01); *A63B 2225/50* (2013.01)

(56) References Cited

U.S. PATENT DOCUMENTS

| | | | | |
|---|---|---|---|---|
| 4,516,772 A * | 5/1985 | Stratton | ............ | A63B 69/0002 473/452 |
| 4,805,913 A * | 2/1989 | Bott | ............ | A63B 69/3667 473/270 |
| 4,813,436 A | 3/1989 | Au | | |
| 5,071,130 A * | 12/1991 | Shofner | ............ | A63B 69/3667 473/218 |
| 5,118,112 A * | 6/1992 | Bregman | ............ | A63B 24/0021 434/252 |
| 5,150,902 A * | 9/1992 | Heisler | ............ | A63B 24/0021 473/409 |
| 5,330,176 A * | 7/1994 | Cagney, Jr. | ............ | A63B 69/0002 473/452 |
| 5,536,004 A * | 7/1996 | Wiseman | ............ | A63B 69/0002 473/417 |
| 5,645,494 A * | 7/1997 | Dionne | ............ | A63B 69/3667 473/270 |
| D399,280 S * | 10/1998 | Griffin | ............ | D21/753 |
| 5,947,833 A * | 9/1999 | Alward | ............ | A63B 69/0002 473/218 |
| 6,102,818 A * | 8/2000 | Hamilton | ............ | A63B 69/0002 473/452 |
| 6,386,996 B1 * | 5/2002 | Foster | ............ | A63B 69/0002 473/422 |
| 6,638,176 B1 * | 10/2003 | Hayes | ............ | A63B 69/3667 473/266 |
| 6,774,349 B2 | 8/2004 | Vock et al. | | |
| 6,906,627 B1 | 6/2005 | Principe | | |
| 7,090,599 B2 * | 8/2006 | Hedgepath | ............ | A63B 69/0002 473/417 |
| 7,125,350 B1 * | 10/2006 | Reason-Kerkhoff | ............ | A63B 69/0002 473/452 |
| 7,186,184 B2 * | 3/2007 | Buck | ............ | A63B 69/3661 473/270 |
| 7,468,010 B2 * | 12/2008 | Du Brock | ............ | A63B 69/0002 473/452 |
| 7,485,071 B2 * | 2/2009 | Edwards | ............ | B32B 25/20 482/907 |
| D602,553 S * | 10/2009 | Wright | ............ | D21/780 |
| D634,385 S * | 3/2011 | Parrish, Jr. | ............ | D21/780 |
| 7,946,935 B2 * | 5/2011 | Hooper | ............ | A63B 69/3661 264/479 |
| 8,221,271 B1 * | 7/2012 | McIntyre | ............ | A63B 69/0002 473/272 |
| 8,226,504 B1 * | 7/2012 | Lozado | ............ | A63B 69/0002 473/422 |
| 9,211,437 B2 * | 12/2015 | Soba | ............ | A63B 21/151 |
| 9,241,589 B2 * | 1/2016 | Saltzman | ............ | A63B 6/00 |
| 9,463,348 B2 | 10/2016 | Connaughton et al. | | |
| 9,492,727 B2 * | 11/2016 | Brossman | ............ | A63B 69/0075 |
| 9,724,581 B2 * | 8/2017 | Tyndall | ............ | A63B 69/0002 |
| D825,701 S * | 8/2018 | Berkley | ............ | D21/780 |
| 10,112,093 B2 * | 10/2018 | Peebles | ............ | A63B 69/0002 |
| 10,471,322 B2 * | 11/2019 | Craig | ............ | A63B 69/0002 |
| 10,493,350 B2 * | 12/2019 | DeMarch | ............ | A63B 71/06 |
| 2002/0160850 A1 * | 10/2002 | Halonen | ............ | A63B 69/3667 473/270 |
| 2005/0143200 A1 | 6/2005 | Hedgepath | | |
| 2006/0211522 A1 * | 9/2006 | Hapanowicz | ............ | A63B 69/0002 473/452 |
| 2006/0258486 A1 * | 11/2006 | Hedgepath | ............ | A63B 69/0002 473/452 |
| 2008/0242437 A1 | 10/2008 | Taylor | | |
| 2009/0181811 A1 * | 7/2009 | Bard | ............ | A63B 69/0002 473/452 |
| 2010/0317452 A1 * | 12/2010 | Lagano | ............ | A63B 22/16 473/272 |
| 2011/0003652 A1 * | 1/2011 | Brend | ............ | A63B 69/00 473/452 |
| 2011/0072581 A1 | 3/2011 | Villa et al. | | |
| 2013/0324382 A1 | 12/2013 | Wilson | | |
| 2015/0231471 A1 * | 8/2015 | Craig | ............ | A63B 69/0062 473/452 |
| 2016/0074708 A1 | 3/2016 | Belhassen et al. | | |
| 2019/0105546 A1 * | 4/2019 | Ferrara | ............ | A63B 69/3667 |

* cited by examiner

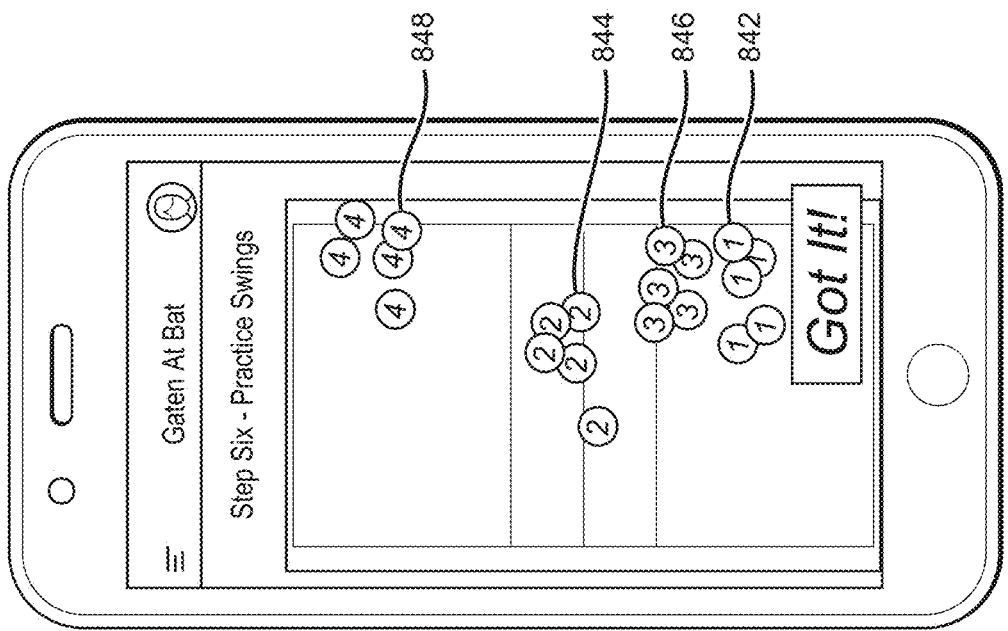
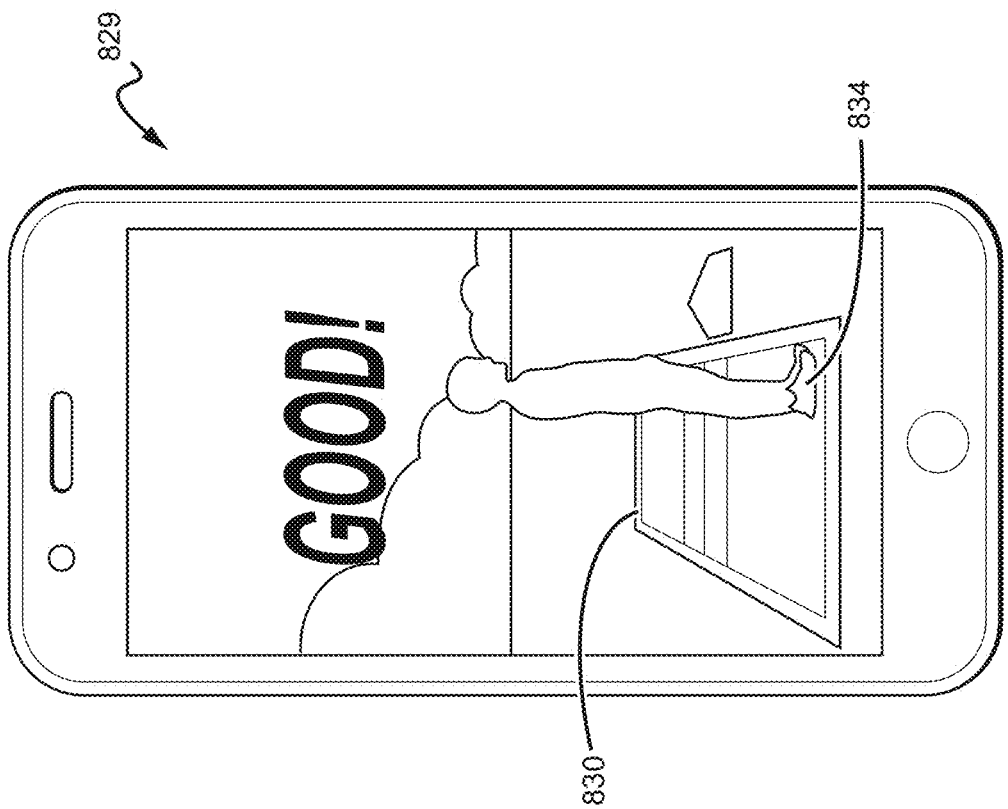

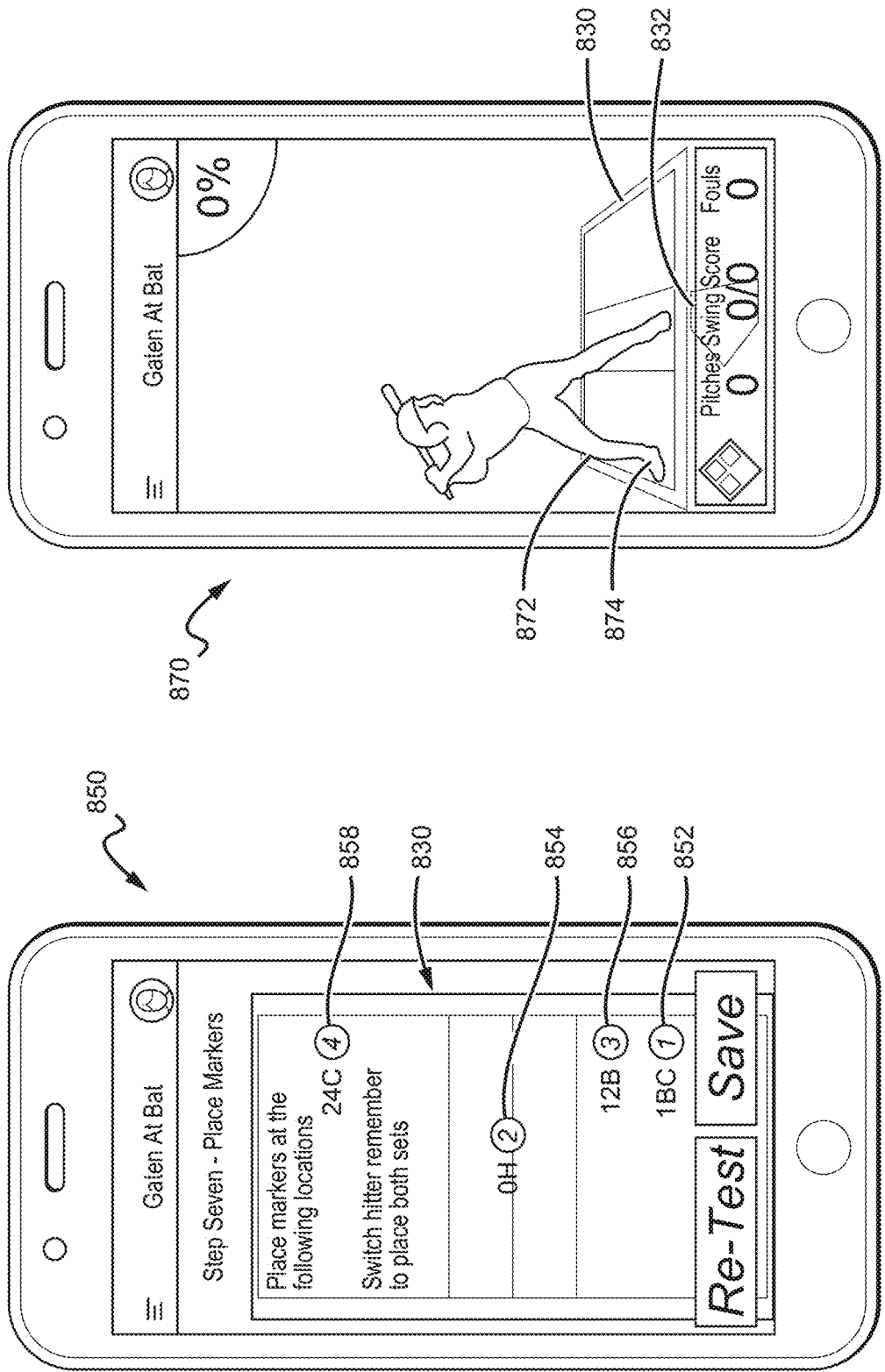

SPORTS TRAINING SYSTEM

RELATED APPLICATION

This application claims priority to U.S. Provisional Application No. 62/568,741, filed on Oct. 5, 2017, which is incorporated by reference herein in its entirety.

BACKGROUND

Field of the Invention

Described herein are devices and systems relating generally to athletic equipment, and specifically to sports training equipment, for example, for competitive sports such as baseball.

Description of the Related Art

Practice mats for sports training generally include features to imitate a partial setting that would be encountered in an athletic event. FIG. 1 shows a replicated configuration of the home plate and batter's boxes for right-handed and left-handed hitters according to Major League Baseball (MLB) measurement standards, which may be found on conventional practice mats for baseball. As shown in FIG. 1, the home plate 110 is six inches to the right of the right-handed batter's box 120 and six inches to the left of the left-handed batter's box 130. The home plate 110 is five-sided, with a front side that is seventeen inches in length and positioned perpendicular to the nearest sides of the right-handed and left-handed batter's boxes 120,130. The front side of the home plate 110 connects the front right and front left sides, which are perpendicular to the front side and extend toward the rear of the home plate 110 by eight and a half inches. The front right and front left sides of the home plate 110 extend to the back right and back left sides, which are equal in length and connect at a point eight and a half inches rearward of the ends of the front right and left sides.

The edges of the home plate 110 connecting the front right side with the back right side and the front left side with the back left side are positioned three feet from the front edge of the batter's boxes 120, 130 and three feet from the back edge of the batter's boxes. The right-handed batter's box 120 is a rectangle six feet long and four feet wide, in which the batter's feet should reside when hitting. Within the right-handed batter's box 120 is the stance/stride zone 122, which is a smaller rectangle sharing the right and rear edges of the batter's box. The stance/stride zone 122 is the area within the batter's box that the hitter generally stays within for optimized positioning. The left-handed batter's box 130 also includes a stance/stride zone 132 and mirrors the right-handed batter's box 120.

One problem with practice mats that only offer a partial imitation of an environment found in a sports-based game is that the training athlete does not receive feedback relating to the performance given. Therefore, the athlete may be repeating improper form and technique without knowing it and, thus, does not improve.

SUMMARY

Described herein are devices and systems relating generally to athletic equipment, and specifically to sports training equipment, for example, for baseball. In some embodiments, the sports training equipment is comprised of a mat and one or more sensors.

The mat provides an area for the user to interact with, for example, practicing techniques of athletic performances on and above, and can comprise markers to imitate an athletic environment, such as home plate and at least a portion of a batter's box according to the Major League Baseball (MLB) measurement standards. In some embodiments, mat sensors are integrated into the mat. In other embodiments, mat sensors are in other components that are removably attached to the mat. In other embodiments, mat sensors are both in the mat and in other components that can be removably attached to the mat. In some embodiments, the mat sensors are position sensors. In some embodiments, at least some of the mat sensors are pressure sensors. In some embodiments, at least some mat sensors are position sensors and at least some mat sensors are pressure sensors.

In some embodiments, one or more hand-held sports instrument sensors can be position sensors that are removably attached to a hand-held sports instrument, such as a baseball bat. Either through direct communication between the bat sensors and the mat sensors or through a separate data collection device, the mat and bat sensors can provide user feedback as to their relative positions.

In some embodiments, the mat does not comprise sensors. Foot markers can be removably attached to the mat to show the user ideal feet positioning. The mat can have charted location markings to reference the specific locations on the mat the foot markers should be. The mat can display at least a portion of the right and left-handed batter's boxes with the home plate in between. In some embodiments, the mat displays at least a portion of only one batter's box with a home plate, wherein the home plate can be partially covered or otherwise altered to display a correctly oriented home plate when the batter's box is used as a right-handed batter's box or a left-handed batter's box. In some embodiments, the mat displays at least a portion of only one batter's box with which a home plate can be positioned relative to the mat.

Some embodiments include a system and method for tracking and analyzing foot positioning of the user while performing a sport or leisure activity. Some embodiments calibrate recommended foot positioning personalized to each user. Some embodiments further display a sport or leisure activity, such as a baseball pitcher pitching a ball, to which the user reacts.

Some embodiments comprise a system, comprising a memory, communicatively coupled to a processor and a camera, the memory having stored therein computer executable instructions configured to implement one or more components of the system. The system can include a play component configured to identify a user's one or more foot positions and compare the one or more foot positions with one or more corresponding recommended foot positions for each athletic performance.

Some embodiments comprise a system comprising a memory, communicatively coupled to a processor and a camera, the memory having stored therein computer executable instructions configured to implement one or more components of the system, including. The system can include: a set-up component configured to create a user account for a user, the set-up component configured to identify correct placement of a mat relative to the camera; a user recognition component configured to identify the feet or shoes of the user; a practice component configured to identify the user's one or more foot positions; an instructional component configured to determine the recommended foot positions at least partially based upon the user's one or more foot positions; and a play component configured to identify a user's one or more foot positions and to compare the one or more foot positions with one or more corresponding recommended foot positions for each athletic performance.

These and other further features and advantages of the invention would be apparent to those skilled in the art from the following detailed description, taken together with the accompanying drawings, wherein like numerals designate corresponding parts in the figures, in which:

BRIEF DESCRIPTION OF THE DRAWINGS

FIG. 17 is a screen display of a user recognition component according to an embodiment of the present disclosure;

FIG. 18A is a screen display of a practice component according to an embodiment of the present disclosure;

FIG. 18B is a screen display of an instructional component according to an embodiment of the present disclosure;

FIG. 19 is a screen display of a play component according to an embodiment of the present disclosure;

DETAILED DESCRIPTION

Figure 1:
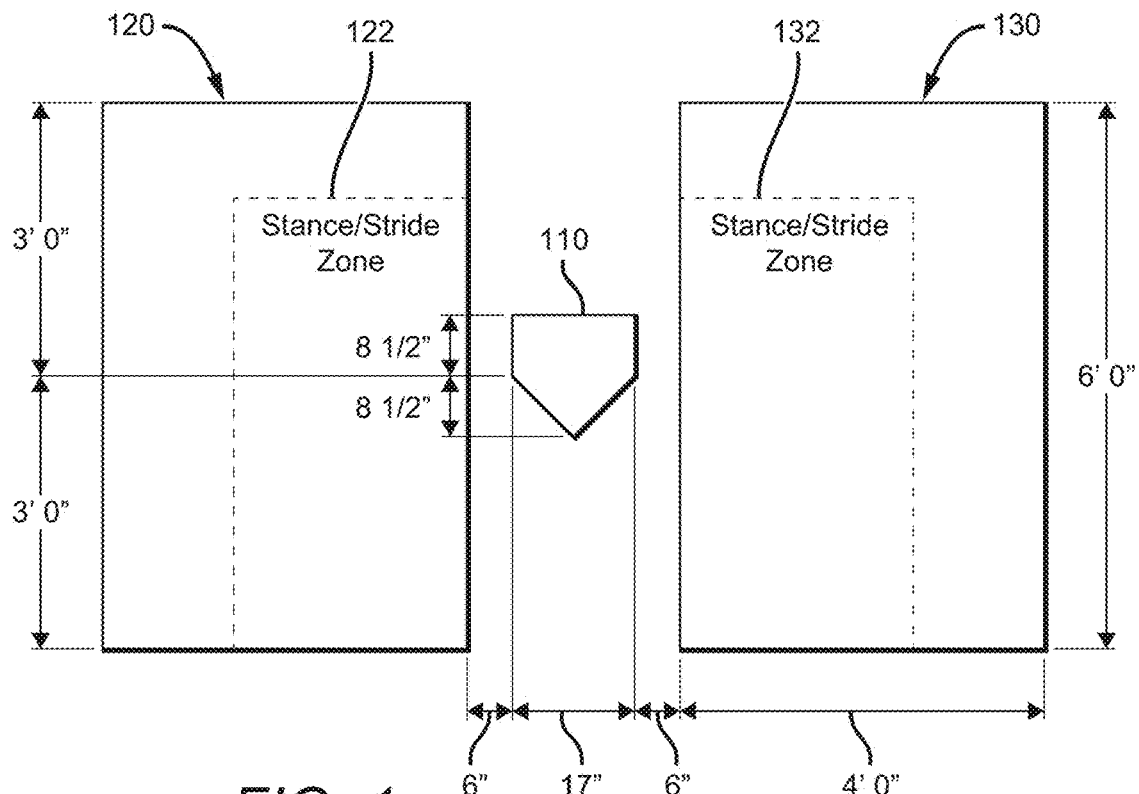
FIG. 1 is a schematic view of a conventional baseball hitter's mat as known within the field.

The present disclosure will now set forth detailed descriptions of various embodiments. These embodiments set forth sports training equipment comprising a mat and one or more sensors. The sports training equipment set forth herein can be used for the training of various sports, for example sports that include a ball and a hand-held sports instrument including, but not limited to, baseball, softball, cricket, badminton, tennis, racquetball, and golf.

One or more hand-held sports instrument sensors can be position sensors that can be permanently or removably attached to a hand-held sports instrument, such as a baseball bat, a softball bat, a racquet, a badminton racquet, a tennis racquet, a cricket bat, and a golf club. Either through direct communication between the hand-held sports instrument sensors and the mat sensors or through the means of a separate data collection device, the mat and hand-held sports instrument sensors provide user feedback as to their relative positions. Through this description the term "swing" and "swings" should be considered as exemplars to "athletic performance" and "athletic performances". For example, any description of a user swinging a bat or other hand-held sports instrument can also include other athletic performance, for example, swinging a golf club.

Throughout this description, the preferred embodiment and examples illustrated should be considered as exemplars, rather than as limitations on the present invention. As used herein, the term "invention," "device," "present invention," or "present device" refers to any one of the embodiments of the invention described herein, and any equivalents. Furthermore, reference to various feature(s) of the "invention," "device," "present invention," or "present device" throughout this document does not mean that all claimed embodiments or methods must include the referenced feature(s).

It is also understood that when an element or feature is referred to as being "on" or "adjacent" to another element or feature, it can be directly on or adjacent the other element or feature or intervening elements or features may also be present. It is also understood that when an element is referred to as being "attached," "connected" or "coupled" to another element, it can be directly attached, connected or coupled to the other element or intervening elements may be present. In contrast, when an element is referred to as being "directly attached," "directly connected" or "directly coupled" to another element, there are no intervening elements present.

Relative terms, such as "outer," "above," "lower," "below," "horizontal," "vertical" and similar terms, may be used herein to describe a relationship of one feature to another. It is understood that these terms are intended to encompass different orientations in addition to the orientation depicted in the figures.

Although the terms first, second, etc. may be used herein to describe various elements or components, these elements or components should not be limited by these terms. These terms are only used to distinguish one element or component from another element or component. Thus, a first element or component discussed below could be termed a second element or component without departing from the teachings of the present invention. As used herein, the term "and/or" includes any and all combinations of one or more of the associated list items.

The terminology used herein is for describing particular embodiments only and is not intended to be limiting of the invention. As used herein, the singular forms "a," "an," and "the" are intended to include the plural forms as well, unless the context clearly indicates otherwise. It will be further understood that the terms "comprises," "comprising," when used herein, specify the presence of stated features, integers, steps, operations, elements, and/or components, but do not preclude the presence or addition of one or more other features, integers, steps, operations, elements, components, and/or groups thereof.

Embodiments of the invention are described herein with reference to different views and illustrations that are schematic illustrations of idealized embodiments of the invention. As such, variations from the shapes of the illustrations as a result, for example, of manufacturing techniques and/or tolerances are expected. Embodiments of the invention should not be construed as limited to the particular shapes of the regions illustrated herein, but are to include deviations in shapes that result, for example, from manufacturing.

Embodiments of the disclosure are described herein with reference to illustrations that are schematic. As such, the actual thickness of elements can be different, and variations from the shapes of the illustrations as a result, for example, of manufacturing techniques and/or tolerances are expected. Thus, the elements illustrated in the figures are schematic in nature and their shapes are not intended to illustrate the precise shape of a region of a device and are not intended to limit the scope of the invention.

It is understood that when a first element is referred to as being "between," "sandwiched," or "sandwiched between," two or more other elements, the first element can be directly between the two or more other elements or intervening elements may also be present between the two or more other elements. For example, if a first element is "between" or "sandwiched between" a second and third element, the first element can be directly between the second and third elements with no intervening elements or the first element can be adjacent to one or more additional elements with the first element and these additional elements all between the second and third elements.

Figure 2:
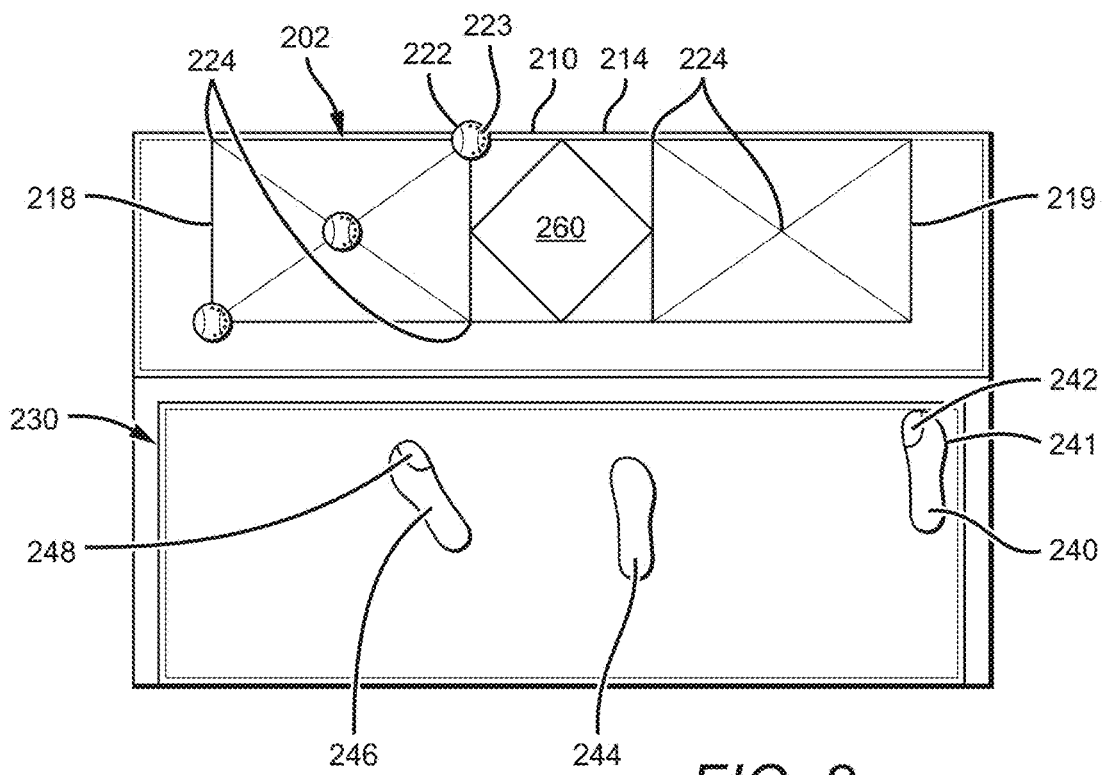
FIG. 2 is a top right side view of a mat and other components according to an embodiment of the present disclosure.

FIG. 2 shows a configuration of a mat 202 incorporating features of the present invention. The mat 202 includes indicators, for example, shapes and colors to imitate the configuration according to MLB regulations that a batter would encounter while hitting, such as the home plate 210 and a portion of the batter's box. The mat 202 in FIG. 2 only includes the stance/stride zone 230, which is the area within the batter's box that batters stay within while hitting, but other embodiments can include a larger portion of the batter's box or the entire batter's box. In the specific embodiment of FIG. 2, the mat 202 only comprises a single stance/stride zone 230, which is configured to be used for both right-handed and left-handed hitters. However, in other embodiments, the mat 202 can comprise two stance/stride zones.

The orientation of the home plate can be changed such that the stance/stride zone is either to the left of the home plate 210 for right-handed hitters or to the right of the home plate 210 for left-handed hitters. The contrasting portion of the mat 202 that represents the home plate 210 is larger than an MLB standard home plate such that a portion can be covered to show a home plate correctly oriented to the right or left side of the stance/stride zone 230. The contrasting portion of the mat 202 that represents the home plate 210, shown in FIG. 2 as a white color, is rectangular, extending the length and width of the regulation size of a home plate. A cover 214 is placed over a part of the contrasting rectangle to form the shape of the home plate 210. FIG. 2 shows the cover 214 positioned to show the home plate 210 correctly oriented in relation to the stance/stride zone 230 for a right-handed hitter. The cover 214 can be of various sizes as long as it is able to cover the portion beyond the perimeter of the home plate 210. In some embodiments, the cover 214 extends to the rear end of the mat 202, covering designs for use when in the mode for the opposite-handed hitter, such as the left-handed contact zone 219 (which is discussed below). The cover 214 can be removably attached to the mat 202 by various attachment instruments known within the field, including but not limited to hook and loop attachments, magnets, or adhesives.

The attachment instruments can be positioned on the mat 202 and/or the cover 214 in such a manner to ensure that the cover 214 is correctly positioned on the mat 202.

In some embodiments, the home plate 210 is removably attached to the mat 202, thus not requiring the cover 214 to alter the orientation of the home plate 210 in relation to the stance/stride zone 230. The home plate 210 can be removably attached to the mat 202 by various attachment instruments known within the field, including but not limited to hook and loop attachments, magnets, or adhesives. The attachment instruments can be positioned on the mat 202 and/or the home plate 210 in such a manner to ensure that the home plate 210 is correctly positioned on the mat 202. In some embodiments, the mat 202 can comprise full or partial batter's boxes for both right-handed and left-handed hitters, such that there is a batter's box on either side of the home plate 210. In some embodiments, the mat 202 can comprise a processor 260 communicably configured with a memory.

The mat 202 can be made from any suitable material that can withstand significant foot traffic. Some example materials include but are not limited to resin, rubber, vinyl, polyurethane, poly vinyl chloride (PVC), polystyrene foam, polymers/copolymer substances, acrylic substances, plastic, leather, metal, glass, fiberglass, wood, cloth or a combination thereof. In some embodiments, the mat 202 is made of pliable materials that can be rolled up for easy transportation and storage. The mat can comprise multiple layers of different materials, with a bottom layer being made from a non-slip material including, but not limited to, rubber. A layer on top of the bottom layer can be a non-skid layer with, for example, a turf or carpet-like texture comprising printed markings. A layer of ink comprising markings can be over the non-skid layer. An optional protective coating layer can be over the non-skid layer as a protectant for the markings, such as a stain and water repellant layer, and to make cleaning the mat easier.

The mat 202 can be formed by any suitable method known in the art, for example, molding, injection molding, stamping and extrusion. While the mat 202 is shown in the figures to be generally rectangular, it is understood that the mat can comprise any number of different shapes and sizes including, for example, any regular polygon or rounded shape. The mat 202 can be battery powered, for example, with a rechargeable battery or it can comprise an AC adapter with an attachable cord to plug into an electrical outlet.

The footpads 240,244,246 are foot markers that can be permanently or removably attached to the mat 202. FIG. 2 shows footpads 240,244,246 that are shaped similar to feet or shoes, although other shapes are possible. In some embodiments, such as the embodiment shown in FIG. 2, the footpads 240,244,246 can be removably attached anywhere on the stance/stride zone 230. The footpads 240,244,246 can be attached securely enough to the mat 202 so that they will not move or become unattached to the mat when a user steps on them. The footpads 240,244,246 can be made of the same material listed herein as acceptable materials for the mat 202 or they can be made of other durable material known within the field. The footpads 240,244,246 can be removably attached to the mat 202 by various attachment instruments known within the field including, but not limited to, hook and loop attachments, spiked bottoms, magnets, adhesives, attachments that snap to a textured mat, clips, or attachment instruments that penetrate the mat and connect to a corresponding receiver positioned underneath the mat.

When using the mat 202, the user stands in relation to the home plate 210 as the user normally would in a game setting and conducts the athletic performance, for example swings the bat. The footpads 240,244,246 are then positioned on the mat 202 according to where the user's feet were positioned. The back footpad 240 is placed where the user's back/anchor foot placement was. This is the position of the rear foot, which can stay in the same position before and during the swing. The stride footpad 244 is placed where the user's front foot was prior to swinging, which is known as the stride/front foot. The stabilizing footpad 246 is placed where the user's front foot was repositioned to during the swing. The footpads 240,244,246 mark the user's general foot placement to improve consistent footwork for the user's athletic form, such as, for example, the user's batting stance before and during the swing.

The footpads 240,244,246 can contain pressure sensors 241 that measure the instantaneous amount of pressure placed on each of the footpads. In some embodiments, the pressure sensors 241 measure the instantaneous general pressure exerted on each whole footpad 240,244,246. In other embodiments, there are multiple pressure sensors 241 in each footpad 240,244,246 that can further determine instantaneous pressure on a specific section of the footpad, thereby allowing the user to have feedback regarding weight distribution within each footpad. Areas within each footpad 240,244,246 containing one or more pressure sensors 241 can include the areas corresponding to the hind foot, the mid foot, the fore foot, and sub-regions within these areas. The footpads 240,244,246 can further comprise toe pressure sensors 242,248 around the big toe areas of the back footpad 240 and the stabilizing footpad 246, respectively. The toe pressure sensors 242,248 measure the instantaneous pressure exerted on the big toe regions of the back footpad 240 and the stabilizing footpad 246, respectively, which is where much of the user's weight is centralized while swinging.

In some embodiments, pressure sensors 241 are in and throughout all or part of the mat 202 rather than the footpads 240,244,246. A processor, for example a computer, identifies the positions of the footpads 240,244,246 on the mat 202 and distinguishes the measurements by the pressure sensors 241 under the footpads from measurements by the remaining pressure sensors in the mat not under the footpads 240,244, 246. One advantage to this configuration is that pressure can still be measured when the user steps partially or fully off the footpads. This allows the same amount of pressure data to be collected had the user only stepped on the footpads 240, 244,246. Further, it allows the user to receive feedback about where and to what extent the foot placement is differing from the positions marked by the footpads 240,244,246.

The mat 202 can comprise a right-handed contact zone 218 and a left-handed contact zone 219. The right-handed contact zone 218 is a rectangular zone adjacent to the front side of the home plate 210 and extending to the front end of the stance/stride zone 230, having a width extending about a baseball's diameter past either side of the home plate 210, and with lines connecting opposite corners. In some embodiments, the right-handed contact zone 218 extends past the front end of the stance/stride zone 230. The right-handed contact zone 218 is the area over which a baseball is generally hit by a right-handed batter and is used as an area on the mat 202 for placing the practice ball 222. The lines connecting the opposite corners within the right-handed contact zone 218 create markers 224 for positioning the practice ball 222. FIG. 2 shows three practice balls 222 at different locations on the right-handed contact zone 218.

In some embodiments, additional markers 224 are within the right-handed contact zone 218 to mark various possible positions for a practice ball 222. The markers 224 are each distinguishable from the other markers 224 by names or other identifiers such as colors or symbols. This allows users to consistently identify each marker 224 among themselves and specify the statistics of each user for a certain marker 224. The left-handed contact zone 219 mirrors the right-handed contact zone 218 on the opposite side of the home plate 210 such that it is adjacent to the front side of the home plate 210 in the left-handed orientation and of comparable dimensions as the right-handed contact zone 218. In some embodiments, the contact zones 218,219 can be of various dimensions, such as comprising a length that does not extend to the front end of the stance/stride zone 230, and thus do not include all the markers 224. The markers that are included in embodiments with various portions of the contact zones 218,219 displayed on the mat 202 can be positioned consistently with the comparable markers 224 in other embodiments, with different portions of the contact zones 218,219 displayed on the mat 202.

In some embodiments, the mat 202 imitates in dimensions and markings an environment that an athlete would find in sports events other than baseball, including but not limited to softball, racquetball, cricket, badminton, and golf. According to the type of sport, the dimensions of the stance/stride zone 230 and contact zones 218,219 can also vary to imitate the environment for the specific sports event.

Each practice ball 222 can be removaby attached to the mat 202 by various attachment instruments known within the field, including but not limited to hook and loop attachments, magnets, or adhesives. The practice ball 222 can imitate a sports ball in shape or lay flat on the mat 202. In some embodiments, such as the embodiment shown in FIG. 2, the practice ball 222 can be two-dimensional or otherwise lay flat on the mat 202. The practice ball 222 can comprise one or more ball position sensors 223 that can measure the distance of a hand-held sports instrument from the area directly above the practice ball 222. In some embodiments, the practice ball 222 comprises multiple ball position sensors 223 along the edge of the practice ball 222 toward the home plate 210. The one or more ball position sensors 223 can measure the angle in a horizontal plane relative to the center of the practice ball 222, which is the location at which the hand-held sports instrument encounters the area directly above the practice ball 222. The ball position sensors 223 can also measure the speed at which the hand-held sports instrument encounters the area directly above the practice ball 222. Thus, a user can swing a hand-held sports instrument, for example a baseball bat or softball bat, in such a manner as if a ball were approaching the user to be contacted by the hand-held sports instrument once the ball were positioned above the location of the practice ball 222. The one or more ball position sensors 223 can then collect data such as the speed and angle at which the hand-held sports instrument would have contacted the ball.

Figure 3:
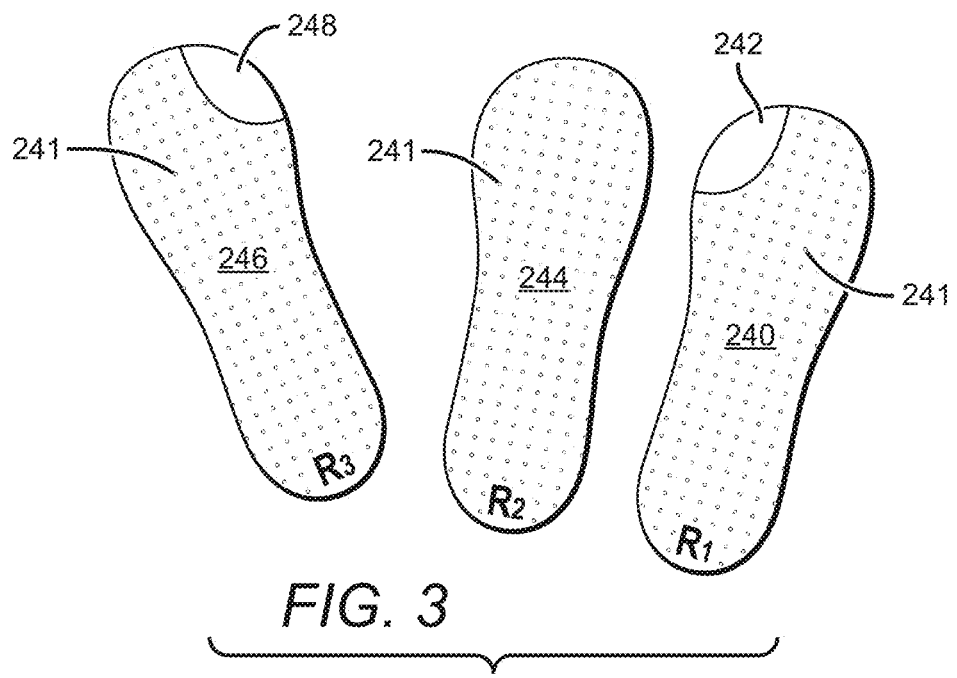
FIG. 3 is a magnified top view of footpads according to an embodiment of the present disclosure.

FIG. 3 shows footpads 240,244,246 for right-handed hitters comprising a back footpad 240 with pressure sensors 241 including a toe sensor 242, a stride footpad 244 with pressure sensors 241, and a stabilizing footpad 246 with pressure sensors 241 including a toe sensor 248. Right-handed hitters can use a right foot-shaped back footpad 240, and left foot-shaped stride and stabilizing footpads 244,246.

Figure 4:
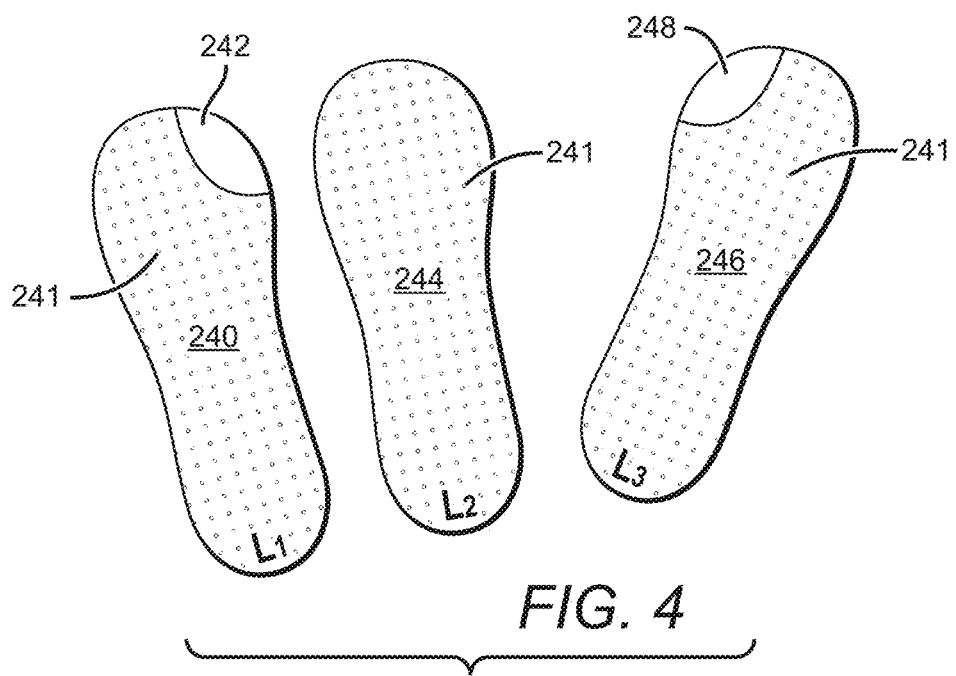
FIG. 4 is a magnified top view of footpads according to an embodiment of the present disclosure.

FIG. 4 shows footpads 240,244,246 for left-handed hitters. The footpads for left-handed hitters can be similar to the footpads for right-handed hitters except with a mirrored shape. FIG. 4 shows a back footpad 240 with pressure sensors 241 including a toe pressure sensor 242, a stride footpad 244 with pressure sensors 241, and a stabilizing footpad 246 with pressure sensors 241 including a toe pressure sensor 248. Left-handed hitters use a left foot-shaped back footpad 240, and right foot-shaped stride and stabilizing footpads 244,246.

Figure 5:
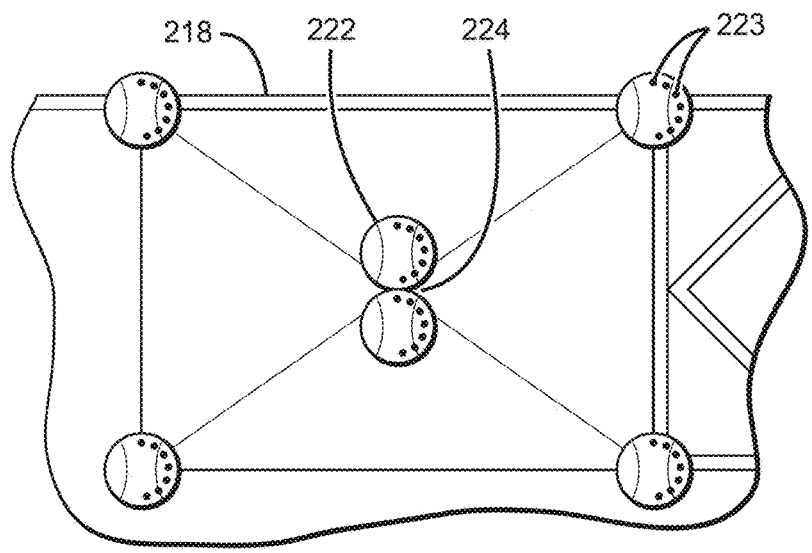
FIG. 5 is a magnified top partial view of a mat and other components according to the embodiment of the present disclosure shown in FIG. 2.

FIG. 5 shows the right-handed contact zone 218 and practice balls 222 on positions determined by the markers 224, with the practice balls oriented such that the ball position sensors 223 are toward the batter. These positions include the four corners along the perimeter of the right-handed contact zone 218 and two of the four center corners created by the two lines connecting opposite corners along the perimeter of the right-handed contact zone 218. The practice ball 222 can be of the size and shape of a standard baseball. In some embodiments, the practice ball 222 can be the size and shape of another sports ball, including but not limited to a softball, a tennis ball, a racquetball ball, a cricket ball, a badminton shuttlecock, and a golf ball.

Figure 6:
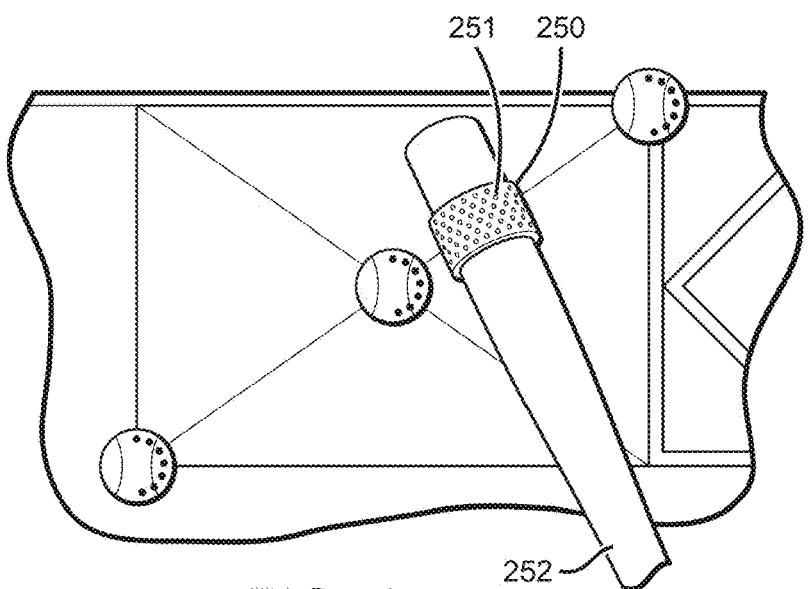
FIG. 6 is a magnified top partial view of a mat and other components according to the embodiment of the present disclosure shown in FIG. 2, and a strap.

In some embodiments, one or more position sensors are removably attached to a hand-held sports instrument. FIG. 6 shows a strap 250 that can be removably attached to a hand-held sports instrument 252. The strap 250 can be made of an elastic material that fits around the hand-held sports instrument 252 and securely tightens around it so that the strap 250 does not change positions on the hand-held sports instrument 252 or fall off the hand-held sports instrument 252 when the hand-held sports instrument 252 is swung. The strap 250 can include one or more position sensors 251 that communicate with the one or more ball position sensors 223 in the practice ball 222, shown in FIG. 5. The one or more sensors 251 in the strap 250 and the ball position sensors 223 measure the distance from the hand-held sports instrument 252 to the area above the practice ball 222.

The position sensors 251 in the strap 250 and the ball position sensors 223 also measure the angle in a horizontal plane relative to the center of the practice ball 222 at which the hand-held sports instrument 252 encounters the area above the practice ball 222 and the instantaneous speed of the hand-held sports instrument 252, including the speed of the hand-held sports instrument 252 as it reaches the area above the practice ball 222. Other types of instruments capable of removably attaching to a hand-held sports instrument 252 and comprising one or more position sensors 251 can also be used instead of the strap 250, including but not limited to, a clip and an adhesive strip.

As discussed below in detail, the mat 202 can comprise a processor such as a microprocessor/microcontroller communicably configured with a memory. The processor can receive and process information from the various sensors.

Figure 7:
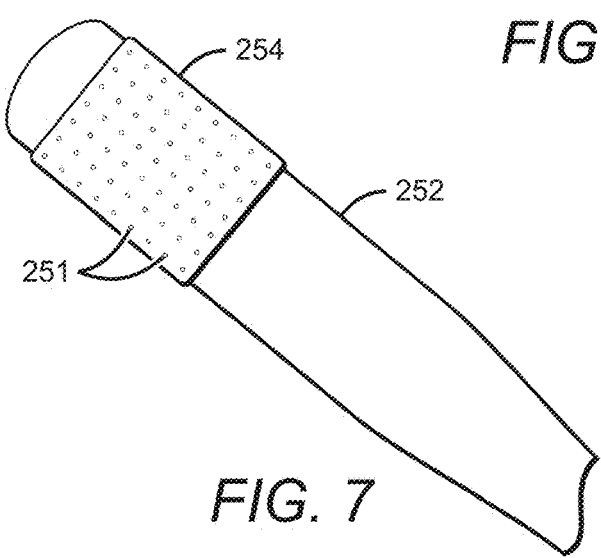
FIG. 7 is a magnified top view of a sleeve according to an embodiment of the present disclosure.

FIG. 7 shows a sleeve 254 that can removably attach to the hand-held sports instrument 252. Similar to the strap 250 shown in FIG. 6, the sleeve 254 comprises one or more position sensors 251 that can make the measurements discussed above. In some embodiments, the sleeve 254 comprises one or more position sensors 251 along a side that is closest to the practice ball 222. In some embodiments, the sleeve 254 comprises position sensors around part or all of the circumference of the sleeve 254 to ensure that a proper reading is still made when the user holds the hand-held sports instrument 252 in a turned position. The sleeve 254 is long enough to cover the area of the "sweet spot" on the hand-held sports instrument 252. It can be made of elastic material that can stretch over the hand-held sports instrument 252 for easy placement on and removal from the hand-held sports instrument 252. In some embodiments, the sleeve 254 can unwrap into an approximately flat component and can wrap into a cylindrical shape via one or more attachment mechanisms including but not limited to hook and loop attachments, magnets, adhesives, or other attachment mechanisms known within the field.

Figure 8A:
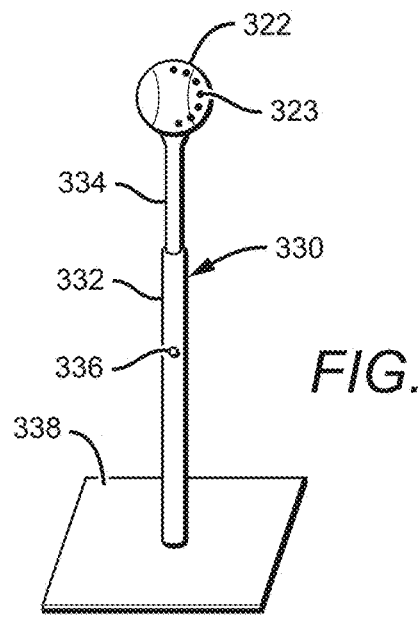
FIG. 8A is a perspective view of a stand and ball according to an embodiment of the present disclosure.

In some embodiments, a three-dimensional ball can be used instead of the practice ball 222 shown in FIG. 2. FIG. 8A shows a three-dimensional ball 322 positioned on the distal end of a stand 330. Unlike with the practice ball 222 where the user swings the hand-held sports instrument 252 over the area above the practice ball 222, the user swings the hand-held sports instrument 252 to contact the three-dimensional ball 322. Similar to the practice ball 222, the three-dimensional ball 322 comprises one or more position sensors 323 to determine the distance between the ball and the hand-held sports instrument 252.

The one or more position sensors 323 on the three-dimensional ball 322 and/or the one or more sensors on the hand-held sports instruments 252 (shown in FIGS. 6 and 7) can also measure the vertical and horizontal angles relative to the center of the ball at which the hand-held sports instrument 252 encounters the three-dimensional ball 322 and the instantaneous speed of the hand-held sports instrument 252, including the speed of the hand-held sports instrument 252 as it contacts the three-dimensional ball 322. The three-dimensional ball 322 can imitate the size, shape, and weight of a ball used in a sporting event, including but not limited to a baseball, softball, tennis ball, cricket ball, racquetball, badminton shuttlecock, and golf ball. The three-dimensional ball 322 can also be lighter and less aerodynamic than a ball used in a sporting event, such as a perforated hollow or semi-hollow ball made from a lightweight and durable material such as plastic or a composite. In some embodiments, the three-dimensional ball 322 can be attached to the stand 330 such that the three-dimensional ball 322 will not come off the stand 330 when hit. This allows the user to not have to retrieve the three-dimensional ball 322 after each hit and makes practice more convenient in environments, such as inside a home.

The stand 330 comprises a lower portion 332 and an upper portion 334. The lower portion of the stand 332 can slide in and out of the upper portion 334 to adjust the height of the stand 330. A coupling mechanism 336 secures the upper portion 334 to the lower portion 332 at the selected height. The coupling mechanism 336 can be any type of securing mechanism known in the field. The stand 330 can comprise sensors that track the height of the stand 330 selected and, thus, can determine the height of the three-dimensional ball 322. At the bottom of the stand 330 opposite the distal end that holds the three-dimensional ball 322 is a base 338 that keeps the stand 330 upright. In some embodiments, the stand 330 comprises a portion along the lower portion 332 and/or the upper portion 334 that easily bends (not shown) to reduce wear on the stand 330 when hit.

Figure 8B:
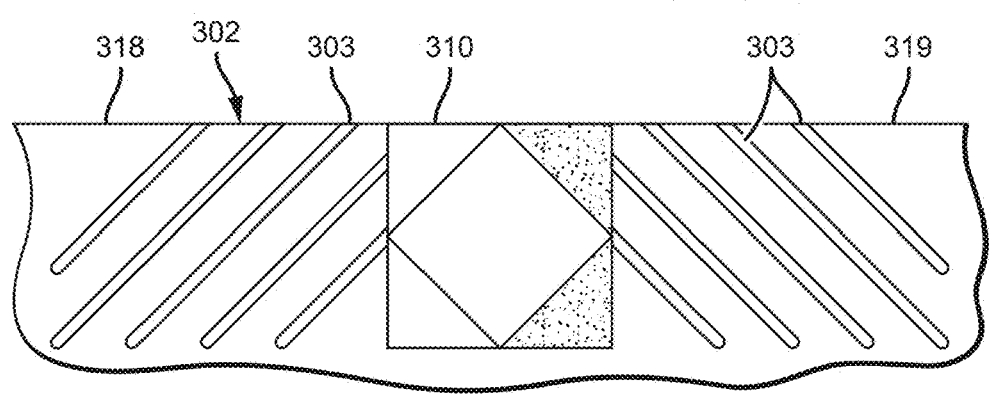
FIG. 8B is a top right side view of a mat according to an embodiment of the present disclosure.

FIG. 8B shows another embodiment of a mat 302, which is similar to the mat 202 described above with the addition of tracks 303 through all or a portion of the thickness of the mat 302. The tracks 303 are on the right-handed and left-handed contact zones 318,319. In the right-handed contact zone 318, the tracks 303 run diagonally in front of the home plate 310 toward the hitter as they approach the front of the right-handed contact zone 318. The tracks 303 in the left-handed contact zone 319 mirror the tracks 303 in the right-handed contact zone 318 such that they also run diagonally in front of the home plate 310 (when in the left-handed hitter orientation) toward the hitter as they approach the front of the left-handed contact zone 319. In some embodiments, the tracks can be straight. In some embodiments, the tracks can be curved. The stand 330 can fit through the tracks 303 such that the base 338 is under the bottom side of the mat 302. The tracks 303 allow the stand 330 to be positioned at numerous locations on the mat 302 by sliding the stand 330 along a track 303 to the desired position, which allows the user to practice hitting balls in many different positions. Sensors in the mat 302 and/or stand 330 can identify the positioning of the stand 330 in relation to the mat 302. Therefore, the area of the mat 302 over which the three-dimensional ball 322 is positioned can be determined. In some embodiments, the tracks have divots (not shown) that the stand 330 can be secured within to create specific positioning options. In some embodiments, the mat 302 can have holes instead of tracks.

In some embodiments, an image of a ball can be displayed for the user instead of the practice ball 222 or the three-dimensional ball 322. In some embodiments, an image of a ball can be shown on a display such as from a projection or on a screen such as a television screen, computer screen, or a wearable screen on the user's head such as a virtual reality screen by a program that is in communication with the display and the other sensors, such as the pressure sensors in the footpads and the one or more position sensors on the hand-held sports instrument 252. The virtual ball can appear to approach the user toward a designated location, including but not limited to a position above one of the markers 224. Once the virtual ball appears close enough to be hit, the user swings the hand-held sports instrument 252. The one or more position sensors on the hand-held sports instrument 252 and the program running to show the image of the ball communicate such that the position of the virtual ball in relation to the position of the hand-held sports instrument 252 is determined. In some embodiments, the angles and speed at which the hand-held sports instrument 252 "contacts" the virtual ball are measured by position sensors in the mat 202 and/or position sensors on the hand-held sports instrument.

Data is recorded such as the vertical and horizontal angles relative to the center of the virtual ball at which the hand-held sports instrument 252 encounters the virtual ball and the instantaneous speed of the hand-held sports instrument 252, including the speed of the hand-held sports instrument 252 as it "contacts" the virtual ball. The program uses the data to calculate the trajectory of the virtual ball based upon the swing of the hand-held sports instrument 252 and any virtual "contact" with the virtual ball. The trajectory of the virtual ball is shown on the display. Through an interface, which can be on a data input device coupled to the processor and specifically for inputting information on a portable computer such as a smartphone or tablet, the user can select different modes saved on the processor or a server connected to the processor such as random positioning for the virtual ball, random speeds for the virtual ball, selected speed ranges for the virtual ball, a specific position for the virtual ball, a specific type of travel for the virtual ball such as a certain type of pitch like a curve ball, and a level of difficultly.

The user can choose certain pitchers to hit against including but not limited to MLB pitchers, minor league pitchers, college pitchers, high school pitchers, and little league pitchers. The pitcher is shown on the display and the virtual ball is thrown by the pitcher. The pitches can be based upon pitches by real-life pitchers. The user can select the type of pitcher or a specific person. The user can select a difficulty level, type of pitch, right-hand or left-hand pitcher, and/or speed. The user can select a pitcher from a certain level or age group to practice against. The user can choose a random selection within one or more of the above categories. Because of the options available to the user, the user can improve by gradually hitting more difficult pitches, whether it be increasing difficulty level, age group of the pitcher, or speed of the pitches for example. In embodiments of the disclosure used to practice for sports other than baseball, such as softball, racquetball, badminton, tennis, cricket, and golf, the pitchers/opponents can be selected from the corresponding sport.

Figure 9:
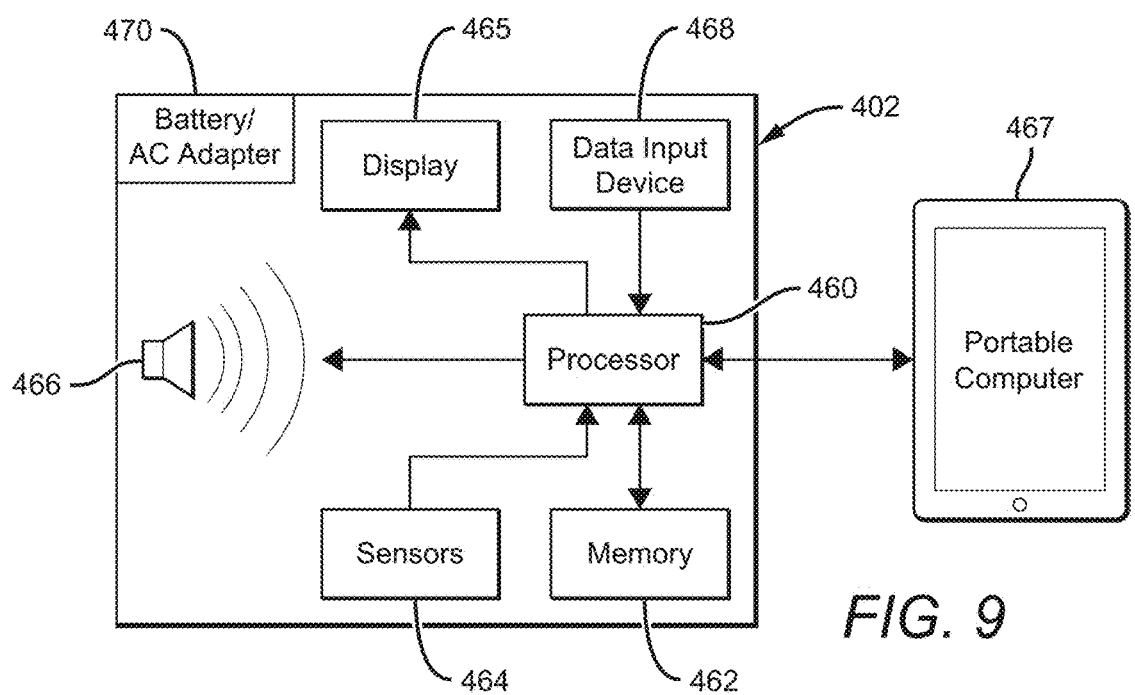
FIG. 9 is a block diagram of a sports training system according to an embodiment of the present disclosure.

FIG. 9 shows a block diagram view of a system comprising a mat 402, which can be similar to embodiments of the mats discussed above, including the mat 202 and the mat 302. The mat 402 can comprise a processor 460 such as a microprocessor/microcontroller communicably configured with a memory 462, the memory 462 having stored therein computer executable instructions configured to collect and process data from the various sensors 464 and user input, send commands to a display 465 such as a projector or screen and one or more speakers 466, and send user statistics to other devices including portable computers 467 and servers via the internet. The processor 460 can be located in or near the home plate and can receive the data collected by the various mat, ball, bat, and/or stand sensors 464 and as input data through a data input device 468 via a short-range wireless interconnection such as Bluetooth®. In some embodiments, the processor 460 collects the data via WiFi. In some embodiments, the processor 460 can collect the data via one or more hardwires. In some embodiments, the data can be collected through a combination of Bluetooth®, WiFi, and one or more hardwires. The collected data is then analyzed. In some embodiments, the processor 460 can be located elsewhere on the mat 402. In other embodiments, the processor 460 is separate from the mat 402. The mat 402 can be battery powered, for example, with a rechargeable battery, or it can comprise an AC adapter with an attachable cord to plug into an electrical outlet.

The processor 460 determines and organizes data including but not limited to the speed of the hand-held sports instrument at the point of actual or theoretical impact with the practice ball 222, three-dimensional ball 322, or virtual ball; the horizontal and vertical angles of the hand-held sports instrument 252 relative to the center of the practice ball 222, three-dimensional ball 322, or virtual ball upon actual or theoretical impact; the trajectory of the practice ball 222, three-dimensional ball 322, or virtual ball were it a standard ball used in a sports event; and the user's weight distribution before swinging and during swinging.

Processed data is then visually presented to the user numerically and/or pictorially. The data can be presented by an output mechanism such as a display, for example, a television screen, a computer screen, a wearable screen such as a virtual reality screen, and a smartphone screen. The information can be sent from the processor 460 via a short-range wireless interconnection such as Bluetooth®. In some embodiments, the information can be sent from the processor 460 via WiFi. In some embodiments, the information can be sent from the processor 460 via one or more hardwires. In some embodiments, the information can be sent from the processor 460 through a combination of Bluetooth®, WiFi, and one or more hardwires. In some embodiments, the weight distribution data is presented numerically, listing the pressure measured at different time intervals. In some embodiments, the weight distribution is presented pictorially on an image of all or part of the mat or an environment that would be encountered in a sports event, such as for example a batter's box. The weight distribution can be color-coded by the degree of pressure measured. For example, where the user's forefoot was positioned might show purple (high pressure) during a swing whereas the middle foot might show yellow (low pressure).

In some embodiments, the trajectory of the practice ball 222, three-dimensional ball 322, or virtual ball were it a standard ball used in a sports event is shown pictorially in an sports event environment, for example a baseball soaring through a baseball field. Data on the trajectory of the ball can also be displayed numerically including, but not limited to the total distance, maximum height, initial speed, and horizontal angle of travel of the ball.

A user can create a user account with a program installed on a computer, such as a portable computer 467, for example, a smartphone or tablet, wherein the user's data is saved to the portable computer 467 and/or a remote server through an internet connection. The data described above can be saved to the user account, including for example, the total hits, total strikes, total foul balls, average distance, average height, and average horizontal angle. The positions of the footpads 240,244,246 can also be recorded as identified by sensors, for example pressure sensors, on the mat 202. The program can include a user interface as discussed above to select different modes, such as random positioning for the virtual ball, random speeds for the virtual ball, selected speed ranges for the virtual ball, a specific position for the virtual ball, a specific type of travel for the virtual ball, such as a certain type of pitch like a curve ball, and a level of difficultly. Through the interface, a user can view additional data including the user's hitting zone, which can be shown on the display and color-coded throughout different regions of the hitting zone based upon the user's hitting average. In some embodiments, the display can additionally show numerically the user's hitting average in the various regions of the hitting zone.

The various sensors can communicate with the program either directly or through the microprocessor/microcontroller 460 (shown in FIG. 2 as 260), including the one or more sensors on the stand and/or the markers to determine the positioning of the ball so the statistics recorded can be categorized according to the position of the ball. One advantage of this communication, for example, is that a user does not have to manually input any statistics and is unable to manipulate the statistics, which improves the reliability of the user's statistics.

A user can select a user's account to remain private or become public for other users to view. Within the network of users, scoreboards and rankings can also be created based upon the user's statistics so that the user can view their statistics against other users within one or more selected criteria including, but not limited to, age group, gender, athletic league, school, athletic team, and geographical region such as town, city, station, region, or country. Rankings can include hitting statistics against certain pitchers and certain types of pitches.

Figure 10:
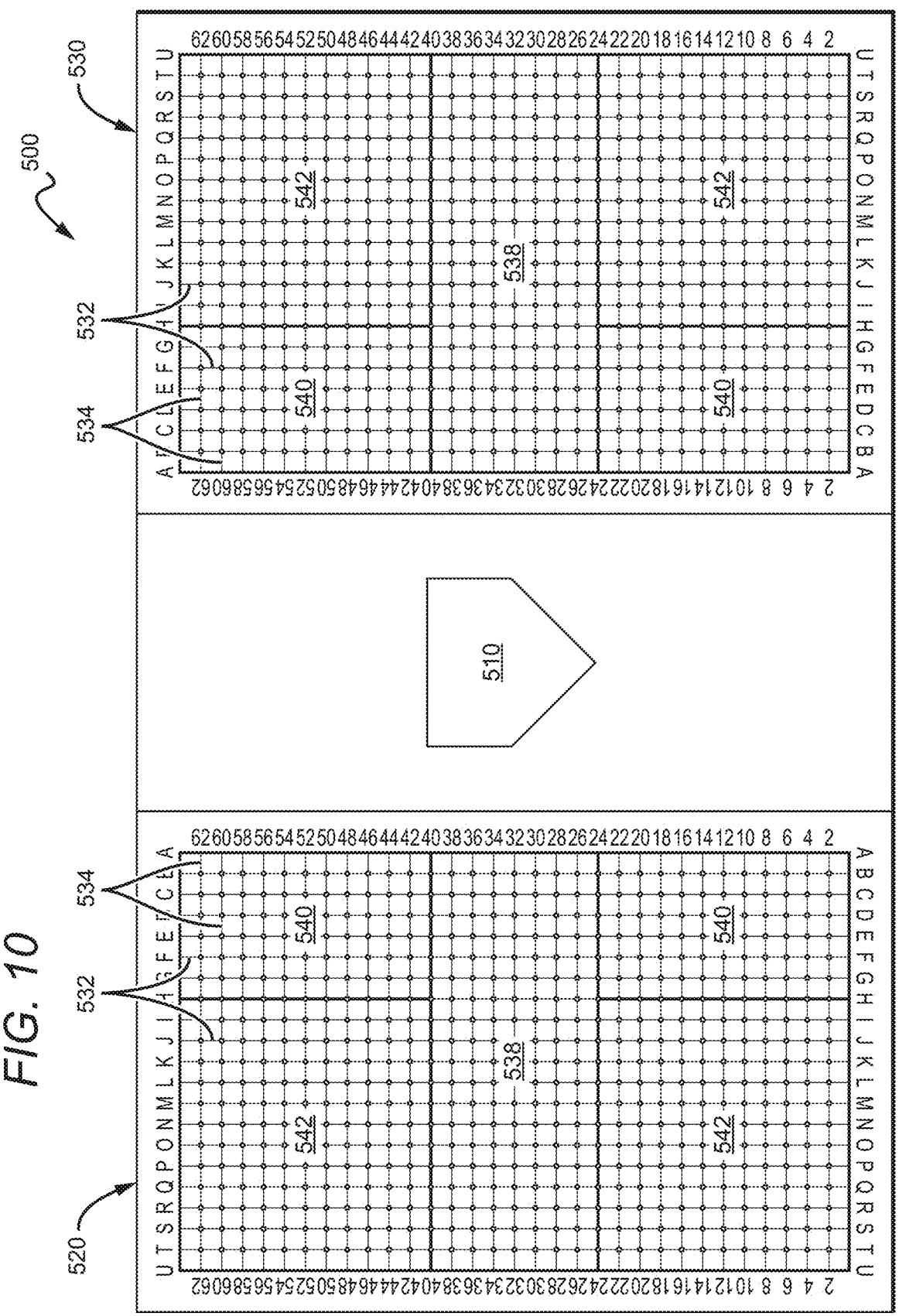
FIG. 10 is a top view of a mat according to an embodiment of the present disclosure.

FIG. 10 shows a top view of another embodiment of a mat 500. The mat 500 can be made of materials and by a process similar to those for the mat 202 shown in FIG. 2. The mat 500 comprises a home plate 510 between a right-handed batter's box 520 and a left-handed batter's box 530. The right and left-handed batter's boxes 520,530 each have markings in and around them to identify relative positions within each box. The markings in and around the left-handed batter's box 530 mirror the markings in and around the right-handed batter's box 520.

As shown in FIG. 10, the markings are displayed in a grid-like layout comprising vertical lines 532 intersecting perpendicular horizontal lines 534 that form rectangles, such as squares. Each square can have the dimensions two inches by two inches. In some embodiments, the squares can have a length less than two inches. In some embodiments, the squares can have a length greater than two inches. In some embodiments, the length and width of the rectangles are not equal. A border four inches wide can surround the grid-like layout, mimicking the four-inch wide border for a standard batter's box. In some embodiments, the border can be greater than four inches wide. In some embodiments, the border can be less than four inches wide.

The vertical and horizontal lines 532,534 are evenly spaced such that the rectangles are the same size. In some embodiments, the vertical and horizontal lines 532,534 can be unevenly spaced such that the rectangles vary in size. Each line can have a unique identifier such as, for example, a numeric, alphabetic, or alphanumeric identifier, which allows the user to identify specific points of intersection between the vertical and horizontal lines 532,534 within the right-handed batter's box 520 and the left-handed batter's box 530. FIG. 10 shows the horizontal line 534 '32' aligns with the center of the home plate 510.

One or more vertical and horizontal lines 532,534 can be used as boundaries to create different zones within the batter's boxes 520,530 comprising one or more rectangles. Each zone can have a unique color for easy identification. For example, FIG. 10 shows a center zone 538 between horizontal lines 534 '24' and '40', which align with the rear and front of the home plate 510, respectively, such that the center zone 538 extends the length of the home plate 510. In some embodiments, the center zone 538 can have a unique color or shade. In some embodiments, the center zone 538 is black. A stance/stride zone 540 extends along the length of the batter's boxes 520,530 on either side of the center zone 538 from the inner edge of the batter's boxes 520,530 nearest the home plate 510 to vertical line 532 'H'. The stance/stride zone 540 marks the ideal area for a batter's feet to remain in relation to the home plate 510. In some embodiments, the stance/stride zone 540 can have a unique color or shade. A peripheral zone 542 extends along the length of the batter's boxes 520,530 on either side of the center zone 538 from the vertical line 532 'H' to the outer edge of the batter's boxes 520,530. The peripheral zone 542 can be identified as a region for the user to not stand in. In some embodiments, the peripheral zone 542 can have a unique color or shade, such that the center zone 538, the stance/stride zone 540, and the peripheral zone 542 each have unique colors or shades.

The stance/stride zone 540 identifies the area in which the user's feet should remain in relation to the home plate 510 to help encourage proper form. The stance/stride zone 540 can be 16 inches wide and 24 inches long on either side of the center zone 538 such that the total length of the stance/stride zone 540, including the portion overlapping the center zone 538, is 64 inches long. In some embodiments, the stance/stride zone 540 can be greater than 16 inches wide. In some embodiments, the stance/stride zone 540 can be less than 16 inches wide. In some embodiments, the total length of the stance/stride zone 540 can be greater than 64 inches. In some embodiments, the total length of the stance/stride zone 540 can be less than 64 inches. In some embodiments, one or more zones can be identified on the mat 500 without vertical lines 532 or horizontal lines 534 identifying specific positions within the one or more zones.

Figure 11:
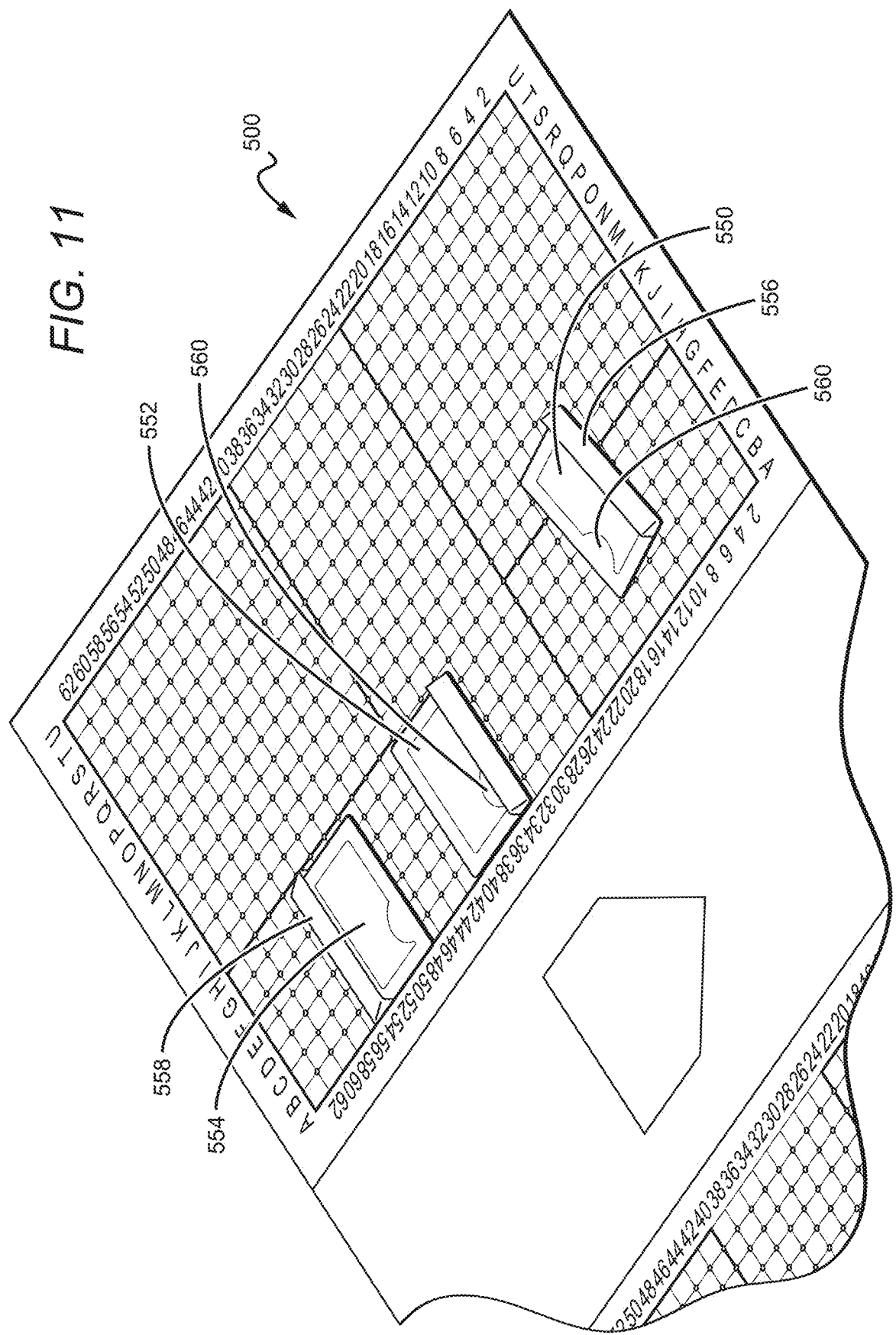
FIG. 11 is a perspective partial view of a mat according to the embodiment of the present disclosure shown in FIG. 10, and footpads.

FIG. 11 shows a close-up top view of the mat 500 with footpads 550,552,554. Similar to the footpads 240,244,246 shown in FIG. 2, the footpads 550,552,554 are foot markers that can be removably attachable to the mat 500. The footpads 550,552,554 can be made of materials such as those described for footpads 240,244,246. The footpads 550,552,554 identify where the user's feet should be placed and comprise the back footpad 550, the stride footpad 552, and the stabilizing footpad 554. The footpads 550,552,554 shown in FIG. 11 do not comprise sensors, although some embodiments can include pressure sensors similar to those discussed for footpads 240,244,246. At least part of the footpads 550,552,554 can be translucent so the user can easily see the markings on the mat 500 for accurate placement of the footpads 550,552,554. In some embodiments, at least part of the footpads 550,552,554 can be transparent. In some embodiments, the footpads 550,552,554 do not comprise translucent or transparent material.

The back footpad 550 and the stabilizing footpad 554 can each comprise a stopper 556,558 to ensure that the user's foot does not extend past the corresponding footpad 550, 554. The stoppers 556,558 can be one or more raised obstructions including, but not limited to, a wall or a raised side extending substantially perpendicular from the base of the back footpad 550 and the stabilizing footpad 554, respectively, and running along the length of the footpads 550,554. The footpads 550,552,554 can have one or more markings 560 to identify where one or more specific parts of the user's foot should be, such as the ball of the foot. In some embodiments, markings 560 corresponding to the shape of the user's foot can be added to the footpads 550,552,554.

The footpads 550,552,554 are attached securely enough to the mat 500 so that they will not move or become unattached to the mat 500 when a user steps on them. The footpads 550,552,554 can be made of the same material listed for the footpads 240,244,246 and can be removably attached to the mat 500 by various attachment mechanisms, such as those listed for the footpads 240,244,246.

In some embodiments, the footpads 550,552,554 are each shaped in a foot pattern approximately the size of the user's feet. In some embodiments, the footpads 550,552,554 are slightly larger than the user's feet. The footpads 550,552,554 can have a texture different than the mat 500 so that the user can feel the footpads 550,552,554 and know if the feet placement is accurate without needing to look at the mat 500 while swinging. In some embodiments, the footpads can be cut to customize the shape to the user's foot.

Figure 12A:
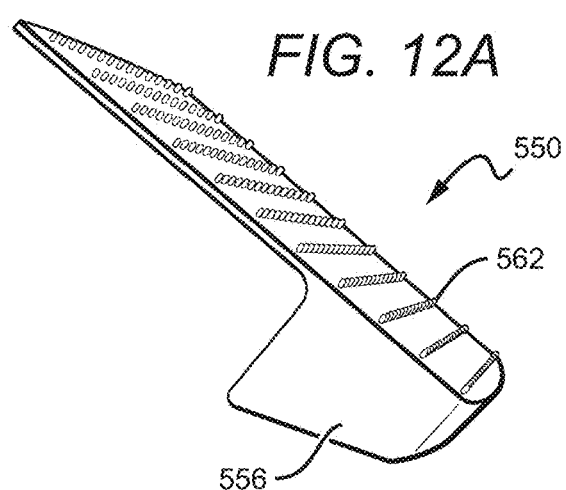
FIG. 12A is a magnified perspective bottom view of a footpad according to the embodiment of the present disclosure shown in FIG. 11.

FIG. 12A shows a side view of the bottom of the back footpad 550 with a stopper 556 and attachment mechanisms 562. In this exemplary embodiment, attachment mechanisms 562 are implemented as spikes, located along the bottom surface of the back footpad 550. The spikes can be pressed into a textured or fibrous top surface of the mat 500 to secure the back footpad 550 to the mat 500. The stride footpad 552 and the stabilizing footpad 554 similarly have attachment mechanisms 562 along the bottom surface. This allows for the footpads 550,552,554 to removably attach to any area within the right-handed batter's box 520 or the left-handed batter's box 530 securely enough to prevent undesired repositioning during use. As discussed above regarding various attachment mechanisms, in some embodiments the bottom of the footpads 550,552,554 can have hook attachments and the mat 500 can have loop attachments.

Figure 12B:
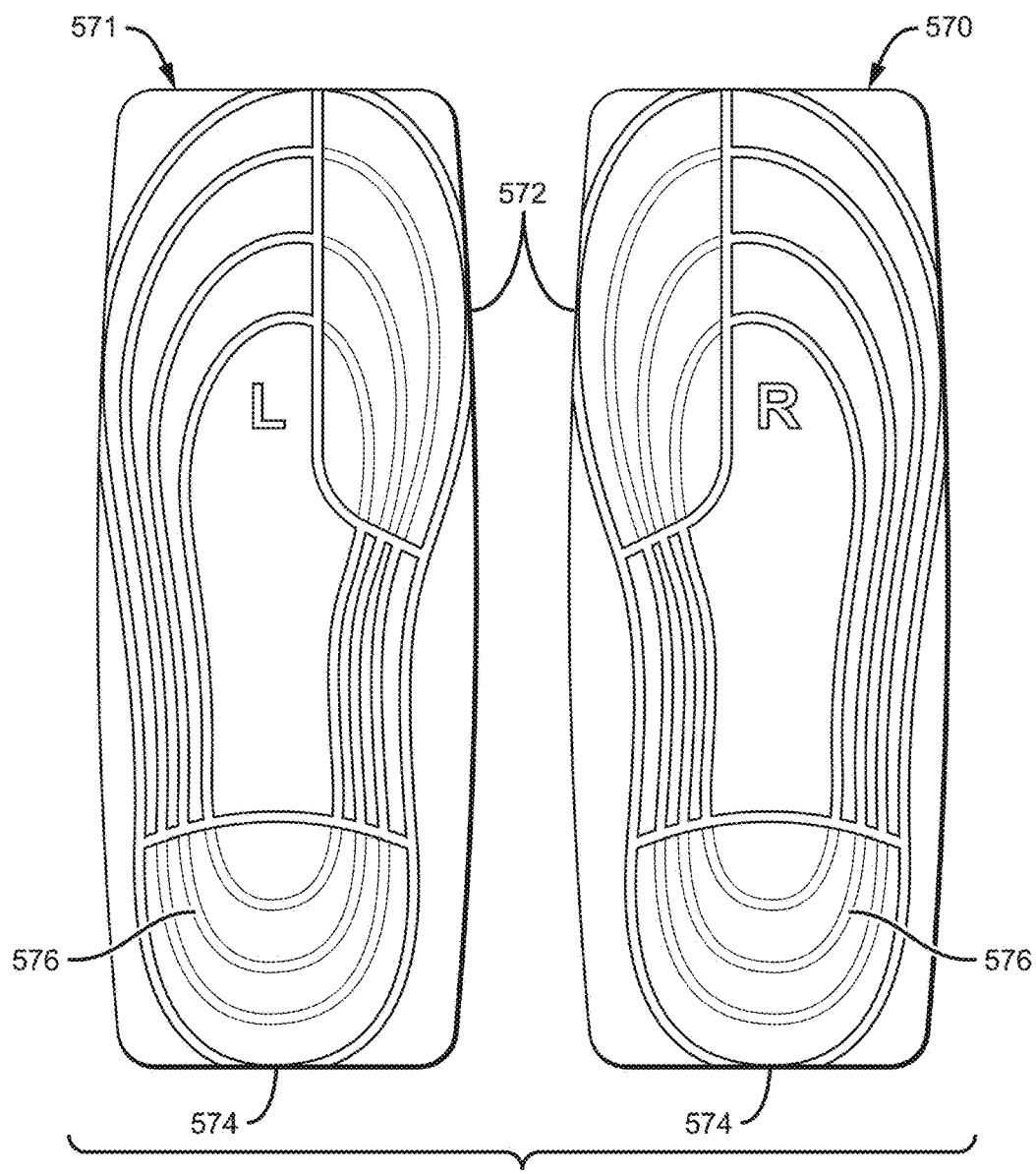
FIG. 12B is a top view of components according to an embodiment of the present disclosure.

FIG. 12B shows stickers 570,571 that can be placed on the top surface of the footpads 550,552,554. The stickers 570 can comprise a right foot sticker 570 and a left foot sticker 571 to be placed on the top surfaces of the back footpad 550 and the stabilizing footpad 554, shown in FIG. 11. For a right-handed batter, the right foot sticker 570 can be placed on the back footpad 550, and the left foot sticker 571 can be placed on the stabilizing footpad 554. For a left-handed batter, the left foot sticker 571 can be placed on the back footpad 550, and the right foot sticker 570 can be placed on the stabilizing footpad 554. The stickers 570 can identify important parts of the foot to place correctly while the user swings for proper technique, such as the big toe 572 and heel 574. The big toe 572 and heel 574 areas can be highlighted on the stickers 570 with a different color than the rest of the stickers 570. In some embodiments, the big toe 572 and heel 574 areas have a different textured surface than the rest of the stickers 570 so that the user can feel if their big toe and heel are contacting the big toe 572 and heel 574 areas. The stickers 570,571 can also have size markings 576 to show where a user should cut out the stickers 570,571 for customizing the sizes of the stickers 570,571 to the size of the user's feet. The stickers 570,571 can be attached to the footpads 550,552,554 by an adhesive or any other attachment mechanism known in the field.

Figure 13A:
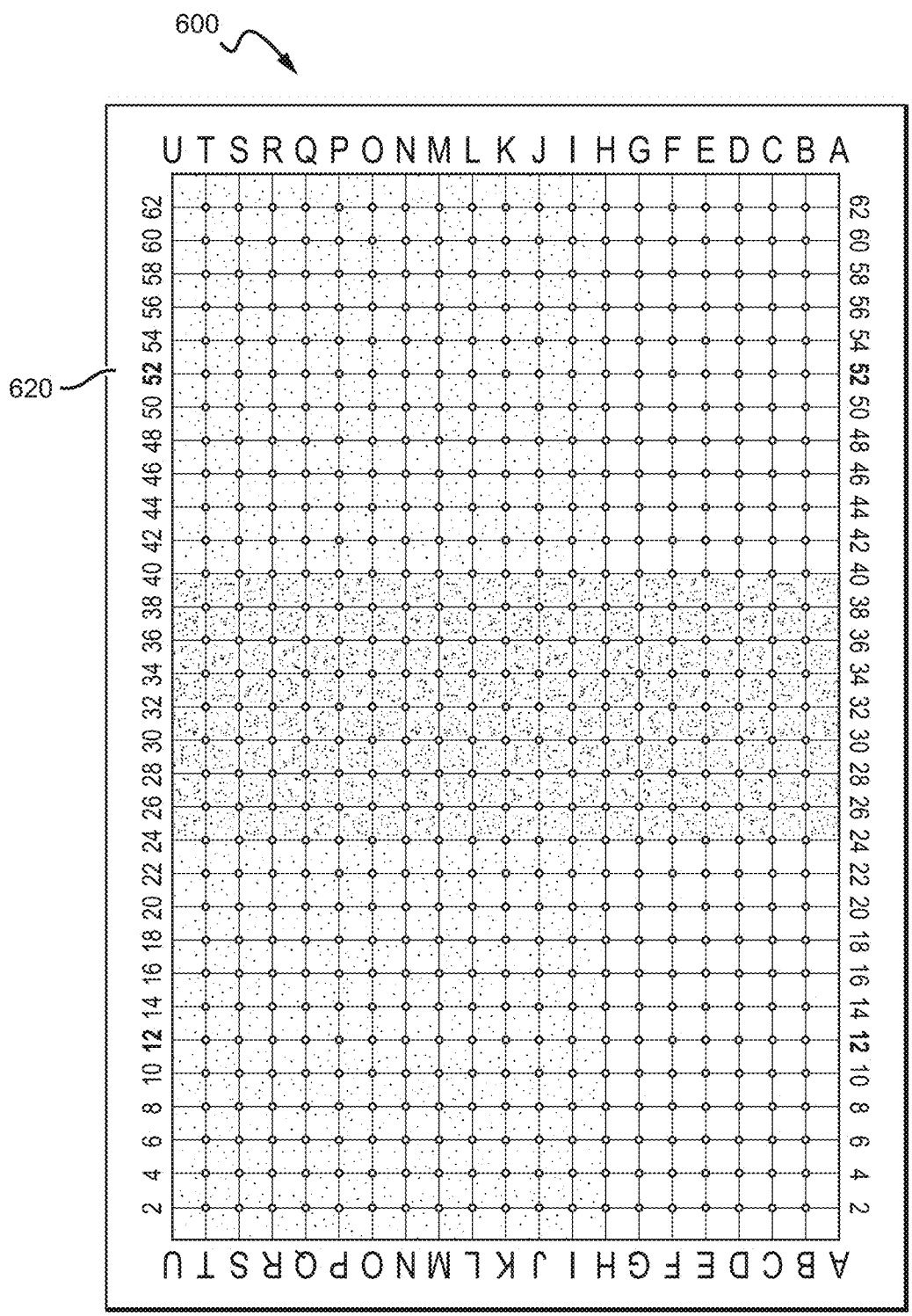
FIG. 13A is a top view of a mat according to an embodiment of the present disclosure.
Figure 13B:
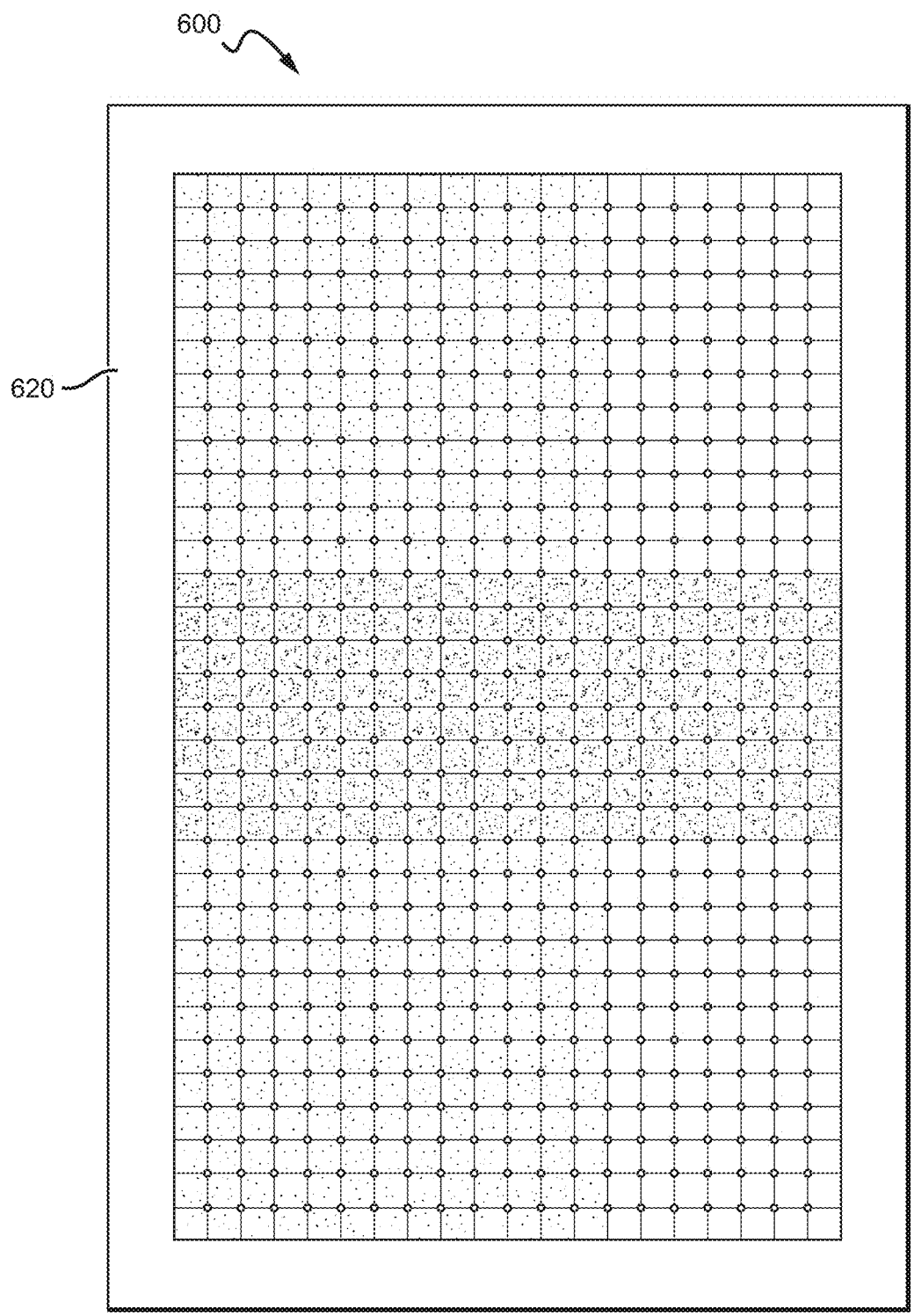
FIG. 13B is a top view of a mat according to an embodiment of the present disclosure.
Figure 13C:
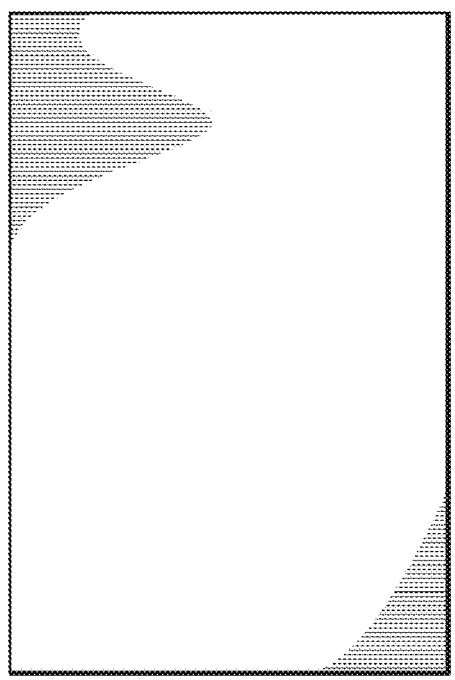
FIG. 13C is a bottom view of a mat according to the embodiment of the present disclosure shown in FIG. 13B.
Figure 13D:
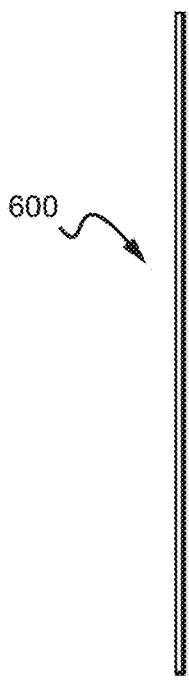
FIG. 13D is a side view of a mat according to the embodiment of the present disclosure shown in FIG. 13B.
Figure 13E:
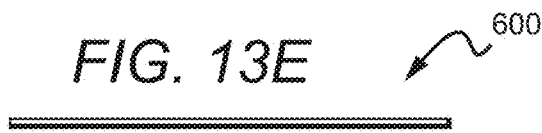
FIG. 13E is a front view of a mat according to the embodiment of the present disclosure shown in FIG. 13B.

FIG. 13A shows a top view of a mat 600 that is similar to the mat 500 shown in FIG. 10, but only has a single batter's box, specifically a right-handed batter's box 620, and does not have a home plate. The mat 600 can be made of materials and in a process similar to those for the mat 202 shown in FIG. 2. A home plate can be positioned next to the mat 600 with the centers of each aligned and separated by 6 inches or any distance according to sport standards. A benefit of the mat 600 is that it is less than half the size of the mat 500, making it more economical and easier to transport and store. Although the mat 600 is shown as a right-handed batter's box 620, it can easily be used as a left-handed batter's box by rotating the mat 600 by 180 degrees and positioning the home plate on the opposite side of the mat 600. In some embodiments, a left-handed batter's box can be a mirror image of the mat 600. In some embodiments, the mat 600 can attach to a home plate or otherwise provide an extension to ensure proper positioning of home plate in relation to the mat 600. FIG. 13B shows an embodiment of the mat 600 without alpha-numeric labeling. FIGS. 13C, 13D, and 13E show bottom, side, and front views of the mat 600, respectively.

Figure 14:
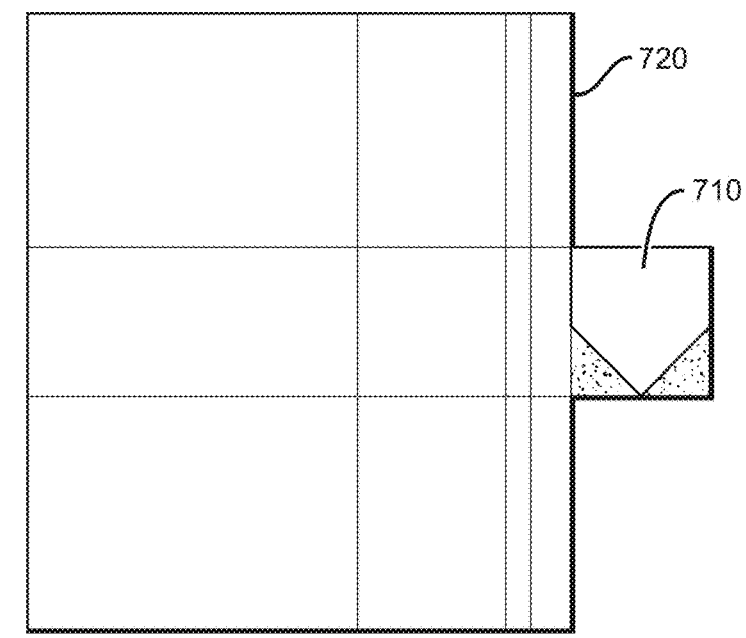
FIG. 14 is a top view of a mat according to an embodiment of the present disclosure.

FIG. 14 is a top view of a mat 700 with a batter's box 720 and a home plate 710. The mat 700 can be made of materials and in a process similar to those for the mat 202 shown in FIG. 2. The home plate 710 can be attached to the mat 700. Although not shown, the mat 700 can have similar markings as the mat 600. In some embodiments, the home plate 710 can be removably attached to the mat 700. In other embodiments, the home plate 710 does not attach to the mat 700, but merely abuts the side of the mat 700. The mat 700 can have an additional area, such as an additional six inches of width running the length of the mat 700 outside of the batter's box 720, which ensures that the home plate 710 is properly spaced from the batter's box 720. In some embodiments, the additional width runs the length of the home plate's 710 abutting side.

In some embodiments, the home plate 710 can be rotated 180 degrees and removably attached to the mat 700 from the opposite side of the home plate 710, which allows the user to use the batter's box 720 for either left-handed or right-handed hitting. In some embodiments, the home plate 710 comprises a cover (not shown) similar to the cover 214 shown in FIG. 2, which can alter the shape of the home plate to appear upside down, and thus right side up in relation to the opposite batter's box. Thus, the batter's box 720 can be used for both right and left-handed batters without repositioning the home plate 710.

In some embodiments, the mats 500, 600, and 700 do not have footpads. In some embodiments, the mats 500, 600, and 700 can have sensors and can be communicably connected to sensors similar to the sensors discussed above pertaining to the mat 202, such as pressure sensors 241. In some embodiments, the sensors are in the mats 500, 600, and 700. In some embodiments, the sensors are in the footpads 550,552,554. In some embodiments, the mats 500, 600, and 700 can have one or more practice balls, similar to the practice balls 222 shown in FIG. 2. The practice balls can have a dome shape with a substantially flat bottom surface to rest against the mats 500,600, and 700 without rolling.

In some embodiments, the program discussed above that can be installed on a computer such as a portable computer 467 shown in FIG. 9, including but not limited to a smartphone, tablet, or any computer that can communicate with a camera, can also be used with mats 500, 600, and 700 that do not comprise sensors. The program can be used for coaching the user where the feet should be placed, for example where the back footpad, the stride footpad, and the stabilizing footpad should be on the mat. The program can also recognize and record the user's feet placement.

Figure 15:
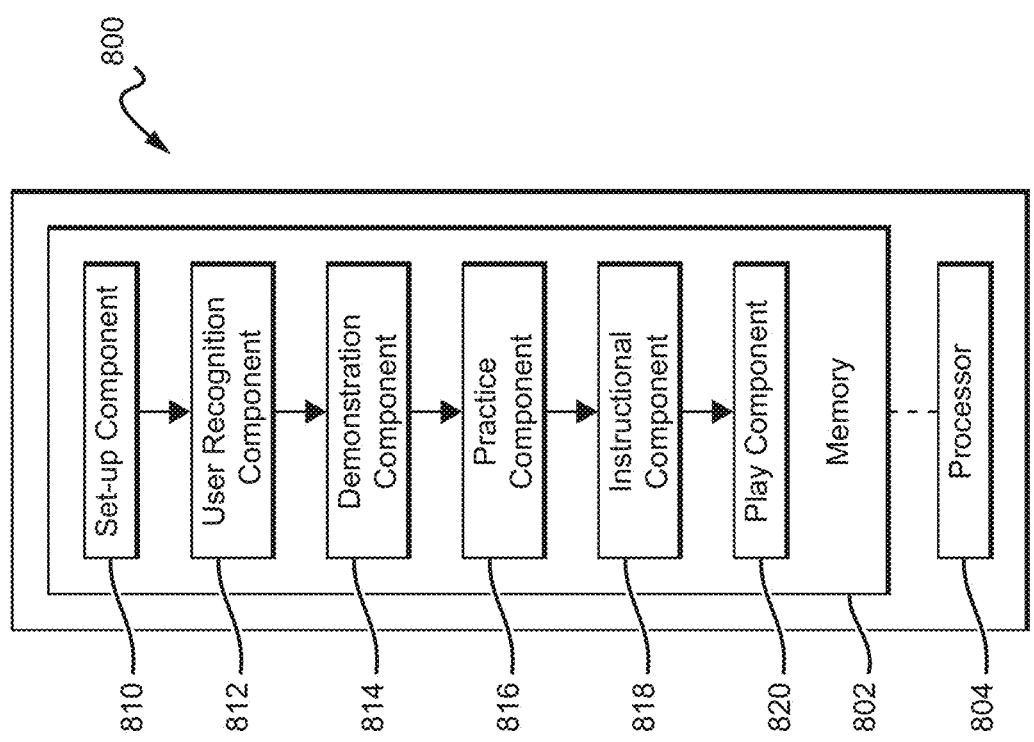
FIG. 15 is a block-diagram of an embodiment of a demonstrative system incorporating features of the present disclosure.

FIG. 15 shows a system 800 that can be used with any of the mats described above. The system 800 can comprise a memory 802 communicatively coupled to a processor 804. The memory can have computer executable instructions, for example stored software, configured to implement one or more components of the system 800. As shown in FIG. 15, the computer executable instructions are configured to implement a set-up component 810, a user recognition component 812, a demonstration component 814, a practice component 816, an instructional component 818, and a play component 820.

The set-up component 810 can present the option for the user to create a user account for the system 800, prompting the user to input name, age, and whether the user bats right-handed, left-handed, or is a switch hitter. In some embodiments, additional information can be entered including, but not limited to, height, weight, and gender. Data collected for the user can be stored in the user account, including the designated foot placement and statistics described below.

The set-up component 810 can be configured to verify acceptable placement of the mat and the computer. Before using one of the mats, the computer is mounted at an elevated position, such as on a tripod in front of the mat with the camera facing the mat, such as about four and a half feet from the mat and at about the user's shoulder height. In some embodiments, the computer can be positioned to the side of the mat, such that the home plate is between the computer and the mat with the computer facing the home plate.

Figure 16:
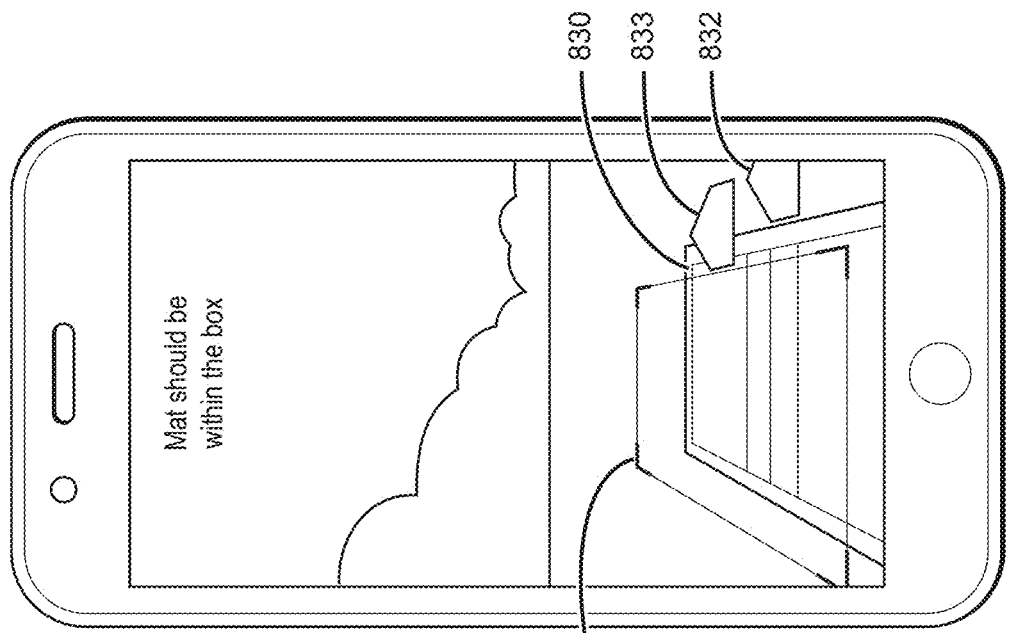
FIG. 16 is a screen display of a set-up component according to an embodiment of the present disclosure.

FIG. 16 shows a screen display 282 of the set-up component 810. The set-up component 810, shown in FIG. 15, can communicate with the camera and can recognize the mat 830 on the ground and can verify that the mat 830 is correctly positioned in front of the camera. If the mat 830 is not correctly positioned, the set-up component 810 can identify the correction required by visually displaying on the computer where the correct mat location 831 is. In some embodiments, the set-up component 810 can also recognize the home plate 832 and can verify if it is correctly positioned in relation to the mat 830. If the home plate 830 is not correctly positioned, the set-up component 810 can identify the correction required by visually displaying on the computer where the correct home plate location 833 is. In some embodiments, the required repositioning of the mat 830 and/or home plate 832 can be communicated audibly by the computer per the set-up component 810 instructions. Once the mat 830 and/or home plate 832 are correctly positioned, the set-up component can present confirmation to the user that this step has been completed.

The user recognition component 812, shown in FIG. 15, can be configured to identify the user's feet or shoes 834 on the mat 830, as shown in FIG. 17 in the screen display 829 of the user recognition component 812. In some embodiments, the user recognition component 812 directs the user to stand by the corner of the mat 830 for the feet or shoes 834 to be identified. Once the camera identifies the user's feet or shoes 834 on the mat 830, the user recognition component 812 can present confirmation to the user that this step has been completed.

The demonstration component 814, shown in FIG. 15, is an optional feature the user can select after the user recognition component 812 has finished, which visually displays an exemplary batter's stance and swing including feet positioning.

The practice component 816 tracks the user's feet placement before and during swinging, for example the position on the mat of the back foot, stride foot, and stabilizing foot. If the user account identifies the user as a switch hitter, the user can be prompted to select which hand the user will be hitting with. The practice component 816 instructs the user to get into batting position and practice a series of swings, for example 10 swings. The user recognition component 812 communicates with the practice component 816 so the user's feet or shoes 834 can be identified and their positions recorded. For switch hitters, the practice component 816 can prompt the user to then repeat the same steps with the opposite hand.

FIG. 18A shows practice swing results from a screen display 840 of the practice component 816, specifically five foot positions each for the rear foot start 842, the front foot start 844, the rear foot finish 846, and the front foot finish 848, recording the foot positions for five practice swings. The rear foot start 842 and the front foot start 844 are where the user's back foot and front foot, respectively, are positioned prior to swinging. The rear foot finish 846 and the front foot finish 848 are where the user's back foot and front foot, respectively, are positioned after swinging.

FIG. 18B shows recommended foot placement from a screen display 850 of the instructional component 818. The practice component 816 can communicate with the instructional component 818, which calculates recommended foot placement on the mat 830 for the recommended rear foot start 852, the recommended front foot start 854, the recommended rear foot finish 856, and the recommended front foot finish 858 based upon the positions of the rear foot start 842, the front foot start 844, the rear foot finish 846, and the front foot finish 848 recorded by the practice component 816. The recommended foot placement can be determined by the average locations of the user's foot placements and an algorithm to improve the user's natural stride. In some embodiments, the practice component 816 can calculate the recommended foot placement for the back foot, stride foot, and stabilizing foot. In some embodiments, the instructional component 818 can visually show the user where on the mat the back footpad 550, the stride footpad 552, and the stabilizing footpad 554 should be placed.

In some embodiments, the instructional component 818 can identify markers on the mat 830 to identify specific positions on the mat 830 that the footpads should be placed, which can be saved in the user account. The user then places the footpads on the mat 830 accordingly. In some embodiments, the instructional component 818 can confirm whether the placement of the footpads is accurate. If the footpads are not accurately placed, the instructional component 818 can instruct the user how to correct the placement. The user can at any time revisit the practice component 816 to reevaluate what the recommended foot placement should be and whether it should be revised.

The user is then ready to play. FIG. 19 shows a screen display 870 of the play component 820 on the computer with the user 872, the mat 830, and the home plate 832 shown on the screen superimposed in a baseball stadium. In some embodiments, the user 872, the mat 830, and the home plate 832 are shown on the screen without being superimposed in another setting. For switch hitter user accounts, the play component 820 can prompt the user 872 to select which hand the user will be batting with. The play component 820 can instruct the user 872 to prepare to swing and when to swing.

In some embodiments, the play component 820 recognizes when the user's feet 874 are in position to swing and can then give a countdown for when the user 872 should swing. In some embodiments, the play component 820 can notify the user of a specific placement of the ball to swing for, for example inside-low or outside-high. The play component 820 can set the camera to record the user while batting so the user can later replay the stance and swing. The play component 820 can also save the foot placement for data collection and analysis, comparing the user's back foot, stride foot, and stabilizing foot placement for each time batting with the recommended foot placement identified by the practice component 816. In some embodiments, the play component 820 can compare the user's foot placement with the footpads. In some embodiments, the play component 820 records and analyzes the position of the user's rear foot start, lead foot start, rear foot finish, and lead foot finish.

The play component 820 can have different modes of play to keep the user engaged. For example, the play component 820 can include awards for the user to win, such as getting a base hit, a double, a triple, a home run, and collecting points. In some embodiments, the play component 820 can include a running tally of successful hits in the form of total number of successful swings and the percentage of successful swings, wherein a successful swing is determined by the user's foot positions being within a determined distance of the recommended foot positions 852,854,856,858. In some embodiments, the extent of the awards are based upon how closely the user's foot positions match the recommended foot positions 852,854,856,858. In some embodiments, an award is given and a successful swing is determined if the user's foot positions are within a determined distance of the footpads 550,552,554.

In some embodiments, the user receives an award only after accomplishing a set number of swings where the user's foot positions are within a predetermined distance from the recommended foot positions or footpads. In some embodiments, the user receives an award only after accomplishing a set number of swings in a row where the user's foot positions are within a predetermined distance from the recommended foot positions or footpads. The level of difficulty can be adjusted, which changes the required distance from the recommended foot placement the user's foot placement must be.

Figure 20:
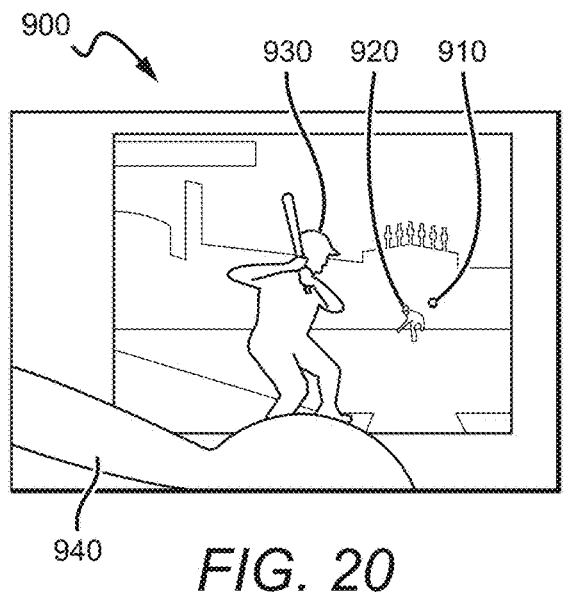
FIG. 20 is an exemplary screen display in a game mode according to an embodiment of the present disclosure.

FIG. 20 shows an exemplary display in a virtual game mode 900. Similar to the virtual ball described above, an image of a ball can be displayed for the user to hit in virtual game mode 900. The computer can be positioned in front of the mat with the screen toward the user such that the user is looking at the screen when in position. An image of a virtual ball 910 can be shown on the screen. The virtual ball can appear to approach the user toward a designated location. In some embodiments, the types of pitches are random. In other embodiments, the types of pitches can be pre-selected. As shown in FIG. 20, the screen can display a pitcher 920 throwing the virtual ball 910 toward the user. The screen can also display the user's avatar 930 in a batting stance and mimicking the position of the user 940, which is determined by the computer's camera. In some embodiments, the screen does not display the user's avatar 930. In some embodiments, the screen displays a game-like environment, for example a baseball stadium.

In some embodiments, a second computer is used to display the virtual balls. Thus, a first computer is tracking the user's stance and foot positioning, while the second computer is set up in front of the user and displaying balls being thrown to the user. The first computer can be communicably connected to the second computer.

A user can select a user's account to remain private or become public for other users to view. Within the network of users, scoreboards and rankings can also be created based upon the user's statistics so that the user can view their statistics against other users within one or more selected criteria including, but not limited to, age group, gender, athletic league, school, athletic team, and geographical region such as town, city, station, region, or country. Rankings can include hitting statistics against certain pitchers and certain types of pitches. Rankings can also include consistency in foot placement. Within the user account, the user can see overviews of foot placement compared to the recommended foot placement.

Figure 21:
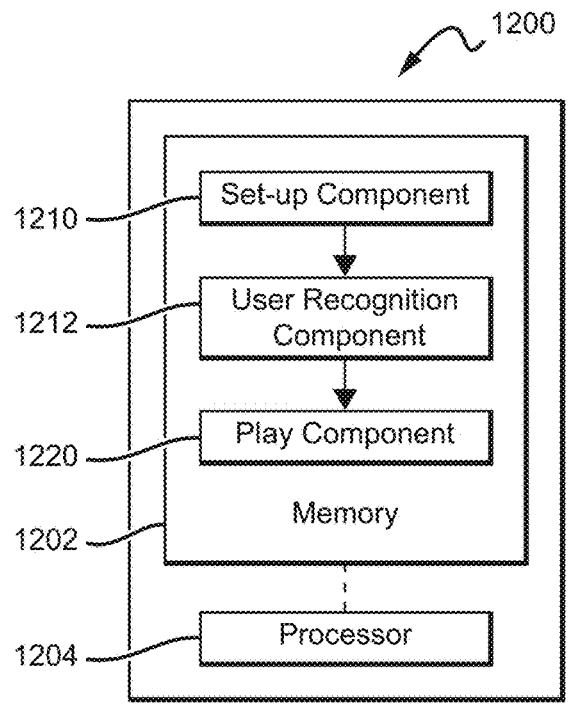
FIG. 21 is a block-diagram of an embodiment of a demonstrative system incorporating features of the present disclosure.
Figure 22:
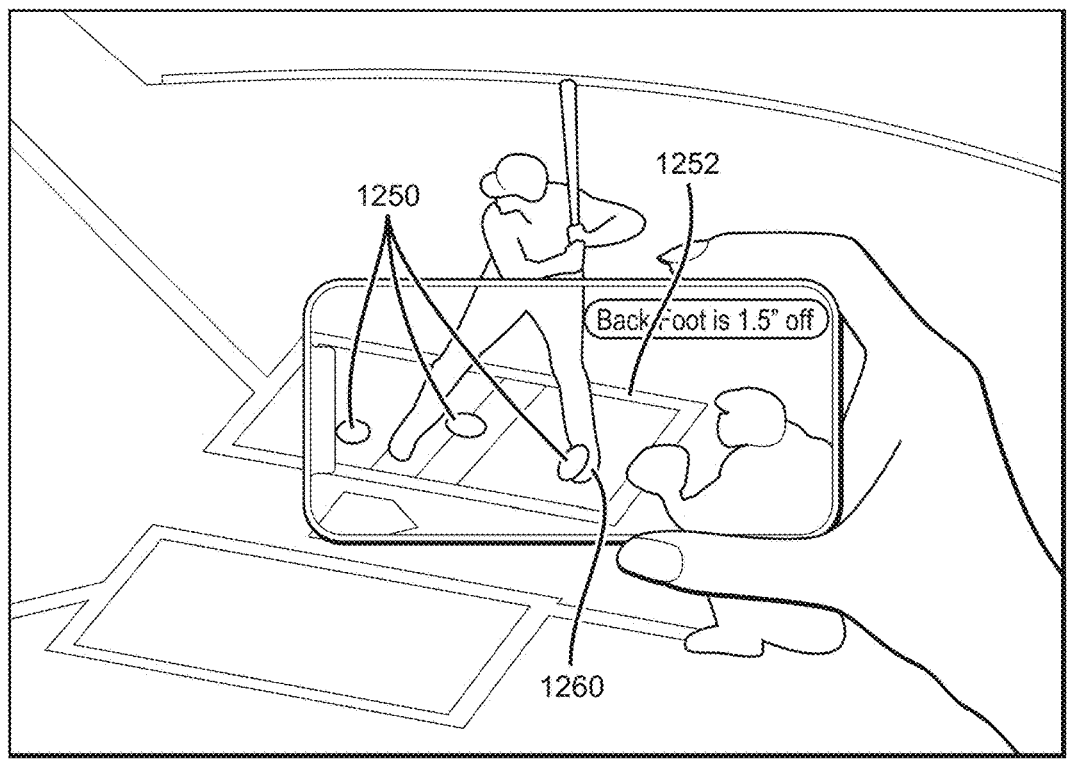
FIG. 22 is an exemplary screen display in a game mode according to an embodiment of the present disclosure.

Another embodiment of the present disclosure is a system 1200 shown in FIGS. 21 and 22. The system 1200 is similar to the system 800, except the system does not need to be used with a mat. Instead, only a home plate is required. The system 1200 can comprise a memory 1202 communicatively coupled to a processor 1204. The memory 1202 can have computer executable instructions, for example stored software, configured to implement one or more components of the system 1200. As shown in FIG. 21, the computer executable instructions are configured to implement a set-up component 1210, a user recognition component 1212, and a play component 1220.

The set-up component 1210 can identify a home plate observed by the computer's camera and establish where the batter's box in relation to the home plate should be. The set-up component 1210 can then have a virtual batter's box displayed on the screen, added to the camera view with the home plate and the rest of the environment observed by the camera. The user can select a user account with already-established recommended foot positions, or another user with public recommended foot positions. Similar to the user recognition component 812 of the system 800, the user recognition component 1212 identifies the feet or shoes of the current user by the home plate.

FIG. 22 shows a screen display of the play component 1220 from FIG. 21, which can display on the screen the locations of the recommended foot positions 1250 for the selected user. The play component 1220 can also superimpose a mat 1252 on the screen. The play component 1220 can compare the superimposed recommended foot positions 1250 with the user's current foot positions 1260, and can determine distinctions between the positions such as the distances between the recommended foot positions and the user's foot positions. The screen display and the gathered data can be recorded and stored in connection with the user.

Similar to the system shown in FIG. 9, the system 800 and the system 1200 can be communicably connected to a display such as a projector or screen and one or more speakers wirelessly or via wire connections for the instructions, data, and interactive portions of the corresponding components described above to be projected visually and audibly.

Figure 23:
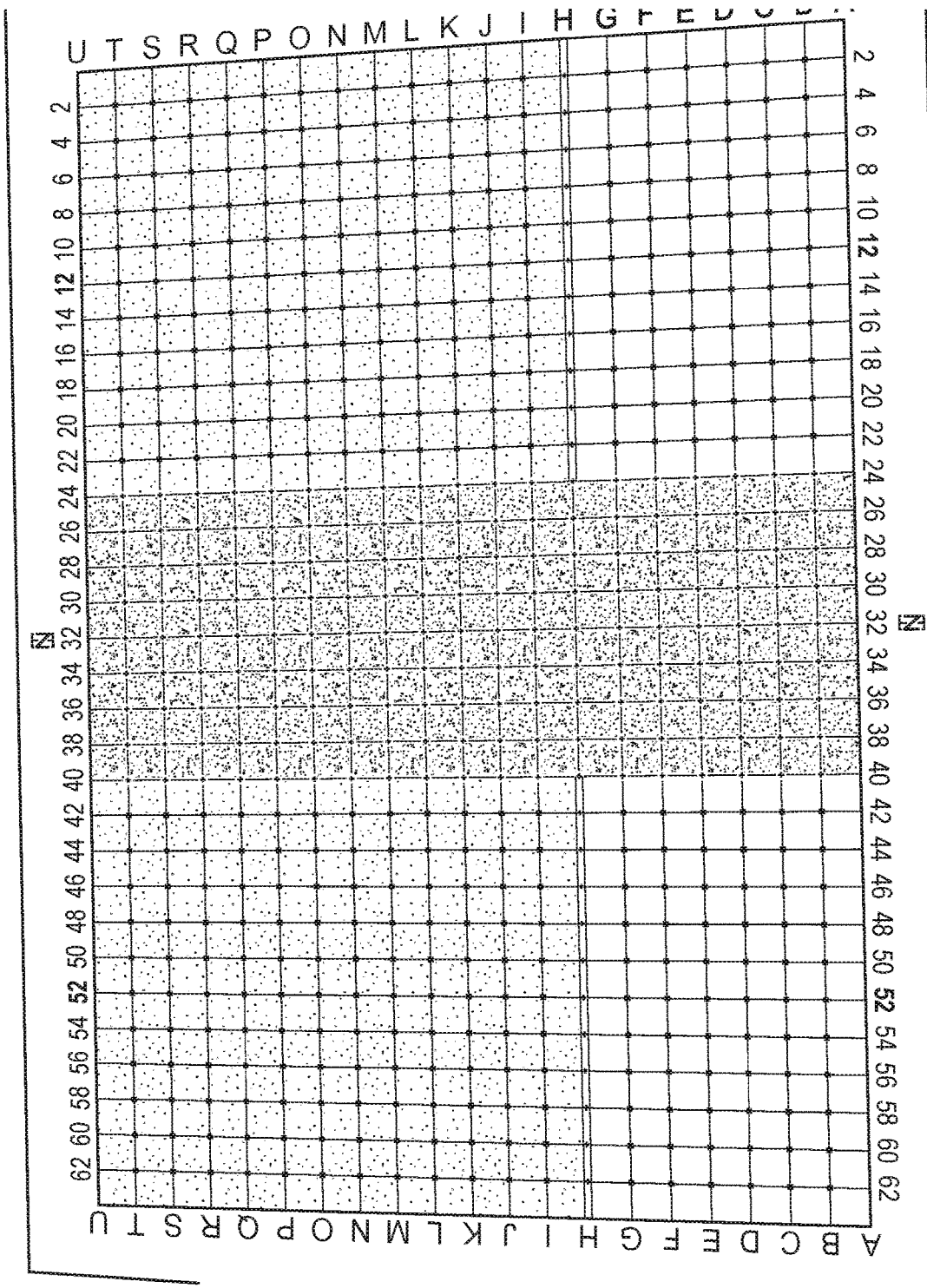
FIG. 23 is a top view of a mat according to an embodiment of the present disclosure.
Figure 24:
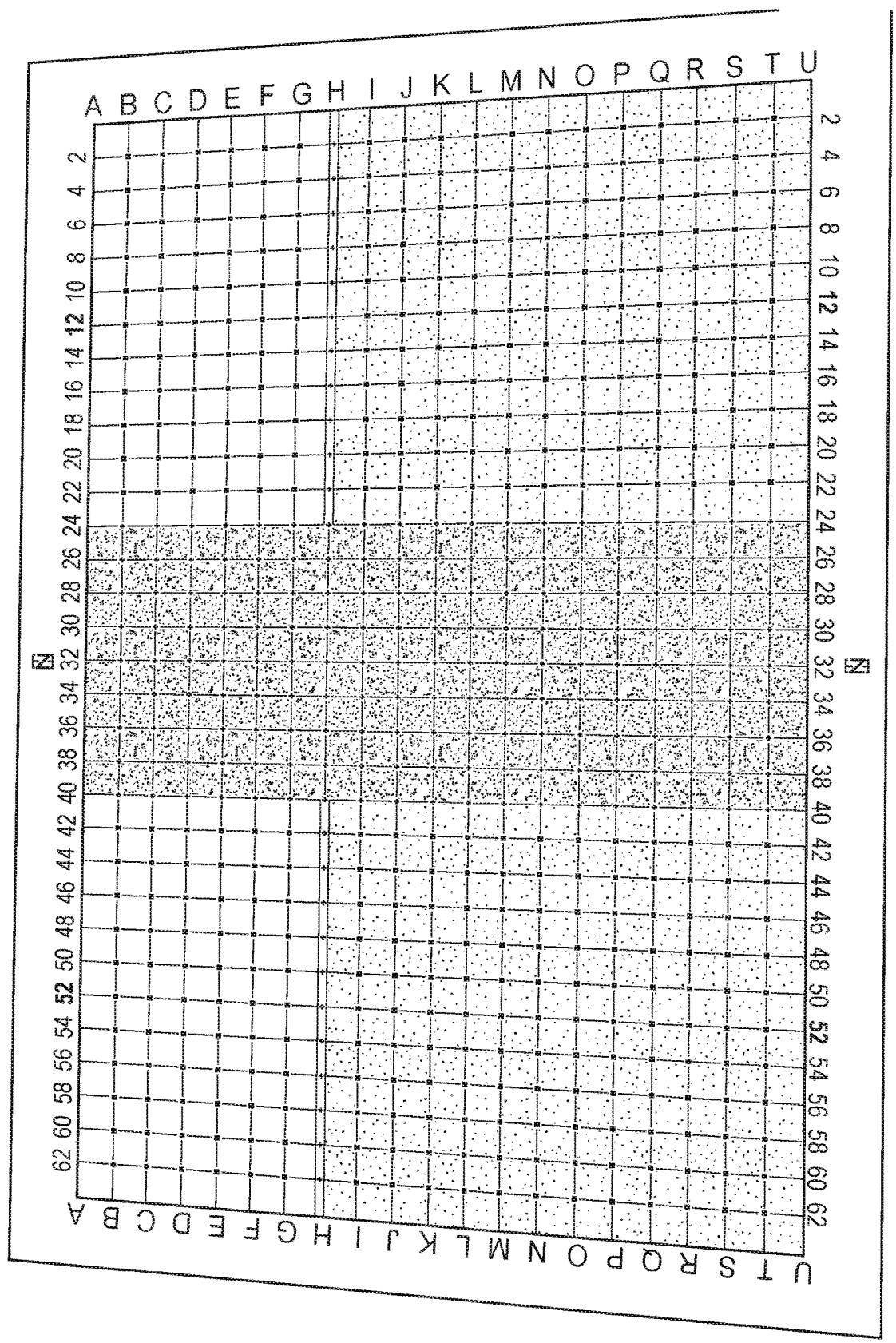
FIG. 24 is a top view of a mat according to an embodiment of the present disclosure.
Figure 25:
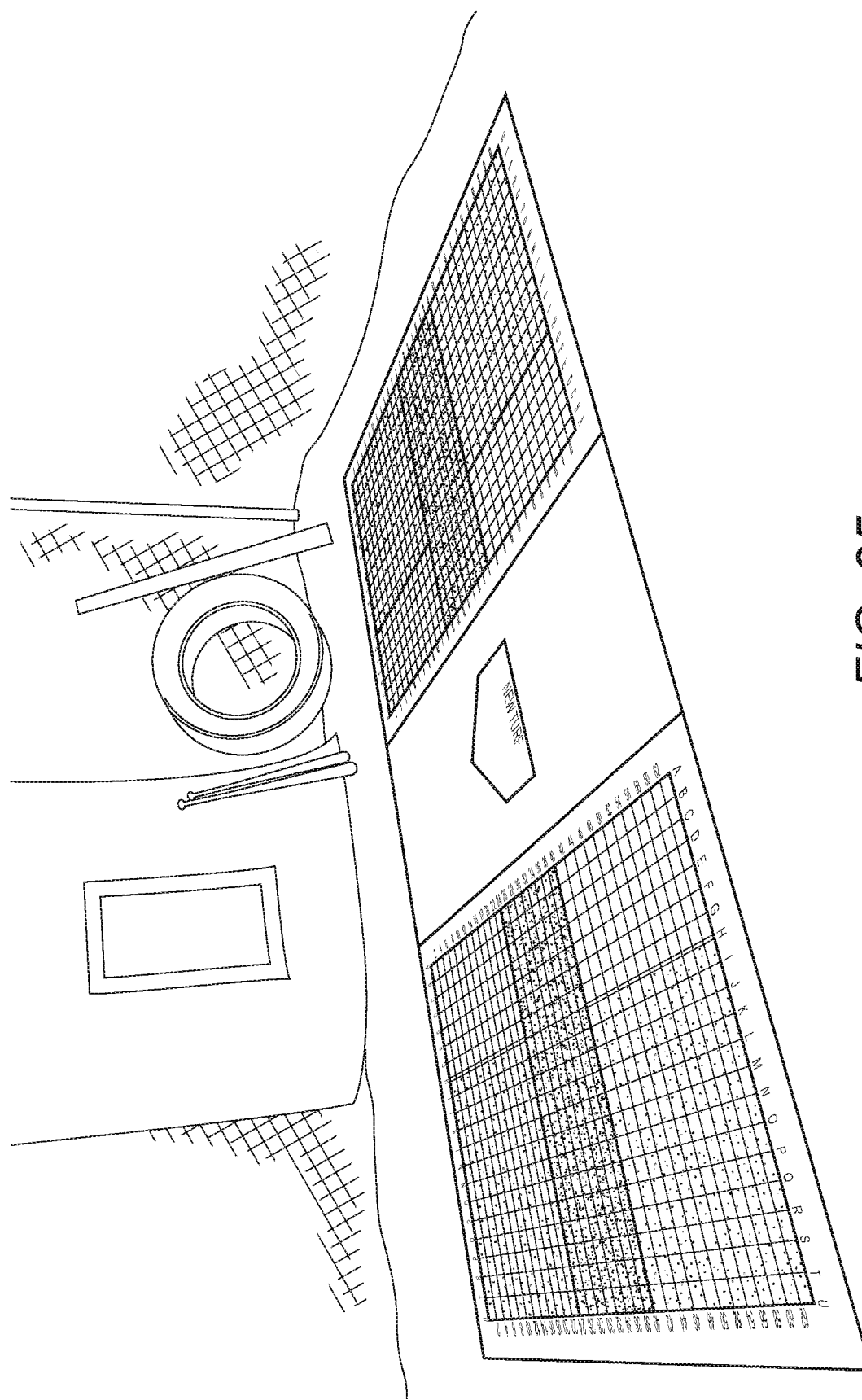
FIG. 25 is a perspective view of a mat according to an embodiment of the present disclosure.

FIG. 23 shows a top view of a mat according to an embodiment of the present disclosure with a left-handed batter's box. FIG. 24 shows a top view of a mat according to an embodiment of the present disclosure with a right-handed batter's box. FIG. 25 shows a perspective view of a mat according to an embodiment of the present disclosure with a right-handed batter's box, a left-handed batter's box, and a home plate.

Although the present invention has been described in detail with reference to certain preferred configurations thereof, other versions are possible. Embodiments of the present invention can comprise any combination of compatible features shown in the various figures and/or descriptions pertaining to various embodiments, and these embodiments should not be limited to those expressly illustrated and discussed. Therefore, the spirit and scope of the invention should not be limited to the versions described above.

The foregoing is intended to cover all modifications and alternative constructions falling within the spirit and scope of the invention as expressed in the claims, wherein no portion of the disclosure is intended, expressly or implicitly, to be dedicated to the public domain if not set forth in any claims.

We claim:

1. An athletic training system, comprising:
    a mat, the mat having a home plate and an adjacent batter's box, the home plate having a rear end and a front end, and wherein the batter's box comprises a plurality of position markers, the plurality of position markers being grid-like markings formed on the mat, including a series of vertical lines intersecting perpendicular horizontal lines to form a plurality of rectangles, and wherein the batter's box has a length with an inner edge adjacent the home plate and an outer edge opposite thereof, with a width spanning between the inner edge and outer edge, and wherein the batter's box includes three visually distinct zones, the three visually distinct zones being a center zone, a stance/stride zone, and a peripheral zone, such that the center zone aligns with the front end and rear end of the home plate and extends between the inner edge and outer edge, and wherein the stance/stride zone extends along the length of the batter's box on either side of the center zone from the inner edge to a vertical line, and wherein the peripheral zone extends along the length of the batter's box on either side of the center zone from the vertical line to the outer edge; and
    three independent footpads having a top side and a bottom surface, the bottom surface having attachment mechanisms configured to removably attach to said mat, and wherein the top side of two of the three footpads comprise a base and a raised side, the base being substantially planar and having a length sufficient to accommodate a user's foot upon the base, and wherein the raised side rises substantially perpendicular from the base, and
    wherein the plurality of position markers identifies positions on the mat where the three footpads are recommended to be placed allowing for improved accuracy of the recommended footpad placement while in use.

2. The athletic training system of claim 1, wherein the attachment mechanisms on the bottom surface of each of the footpads are selected from a group consisting of a plurality of spikes and hook and loop fasteners, such that each footpad is adapted to be affixed independently at any location within the batter's box.

3. The athletic training system of claim 1, wherein said footpads are at least partially translucent.

4. The athletic training system of claim 1, wherein said plurality of footpads comprise one or more pressure sensors.

5. The athletic training system of claim 4, further comprising a processor operatively coupled to said one or more pressure sensors.

6. The athletic training system of claim 5, wherein said processor is communicably configured with a memory, wherein said memory is configured to store data collected from said one or more pressure sensors.

7. The athletic training system of claim 6, wherein said processor is configured to send said data to a computer.

8. An athletic training system, comprising:
    a mat, the mat having a home plate and an adjacent batter's box, the home plate having a rear end and a front end, and wherein the batter's box comprises a plurality of position markers, the plurality of position markers being grid-like markings formed on the mat, including a series of vertical lines intersecting perpendicular horizontal lines to form a plurality of rectangles, and wherein the batter's box has a length with an inner edge adjacent the home plate and an outer edge opposite thereof, with a width spanning between the inner edge and outer edge, and wherein the batter's box includes three visually distinct zones, the three visually distinct zones being a center zone, a stance/stride zone, and a peripheral zone, such that the center zone aligns with the front end and rear end of the home plate and extends between the inner edge and outer edge, and wherein the stance/stride zone extends along the length of the batter's box on either side of the center zone from the inner edge to a vertical line, and wherein the peripheral zone extends along the length of the batter's box on either side of the center zone from the vertical line to the outer edge; and the length of the batter's box on either side of the center zone from the vertical line to the outer edge; and three independent footpads having a top side and a bottom surface, the bottom surface having attachment mechanisms configured to removably attach to said mat, and wherein the top side of two of the three footpads comprise a base and a raised side, the base being substantially planar and having a length sufficient to accommodate a user's foot upon the base, and wherein the raised side rises substantially perpendicular from the base, and wherein the plurality of position markers identifies positions on the mat where the three footpads are recommended to be placed allowing for improved accuracy of the recommended footpad placement while in use.

9. The athletic training system of claim 8, further comprising a processor operatively coupled to said one or more pressure sensors.

10. The athletic training system of claim 9, wherein said processor is communicably configured with a memory, wherein said memory is configured to store data collected from said one or more pressure sensors.

11. The athletic training system of claim 10, wherein said processor is configured to communicate with a screen and display said data on said screen.

12. The athletic training system of claim 8, wherein the attachment mechanisms on the bottom surface of each of the footpads are selected from a group consisting of a plurality of spikes and hook and loop fasteners, such that each footpad is adapted to be affixed independently at any location within the batter's box.

* * * * *